(12) United States Patent
Nurmikko et al.

(10) Patent No.: US 7,280,870 B2
(45) Date of Patent: Oct. 9, 2007

(54) OPTICALLY-CONNECTED IMPLANTS AND RELATED SYSTEMS AND METHODS OF USE

(75) Inventors: Arto V. Nurmikko, Providence, RI (US); John P. Donoghue, Providence, RI (US); J. Christopher Flaherty, Topsfield, MA (US); William R. Patterson, III, Rehoboth, MA (US)

(73) Assignee: Brown University Research Foundation, Providence, RI (US)

( * ) Notice: Subject to any disclaimer, the term of this patent is extended or adjusted under 35 U.S.C. 154(b) by 605 days.

(21) Appl. No.: 10/453,785

(22) Filed: Jun. 4, 2003

(65) Prior Publication Data

US 2004/0015211 A1    Jan. 22, 2004

Related U.S. Application Data

(60) Provisional application No. 60/385,761, filed on Jun. 4, 2002.

(51) Int. Cl.
*A61N 1/375* (2006.01)
*G02B 6/36* (2006.01)

(52) U.S. Cl. .......................................... 607/37; 385/88
(58) Field of Classification Search ................ None
See application file for complete search history.

(56) References Cited

U.S. PATENT DOCUMENTS

| | | | |
|---|---|---|---|
| 3,837,339 A | 9/1974 | Aisenberg et al. | |
| 3,850,161 A | 11/1974 | Liss | |
| 4,055,175 A | 10/1977 | Clemens et al. | |
| 4,146,029 A | 3/1979 | Ellinwood, Jr. | |
| 4,294,245 A | 10/1981 | Bussey | |
| 4,360,031 A | 11/1982 | White | |
| 4,432,363 A | 2/1984 | Kakegawa | |
| 4,461,304 A | 7/1984 | Kuperstein | |
| 4,495,917 A | 1/1985 | Byers | |
| 4,633,889 A | 1/1987 | Talalla et al. | |
| 4,690,142 A | 9/1987 | Ross et al. | |
| 4,837,049 A | 6/1989 | Byers et al. | |
| 4,865,048 A | 9/1989 | Eckerson | |
| 4,878,913 A | 11/1989 | Aebischer et al. | |
| 4,883,666 A | 11/1989 | Sabel et al. | |
| 4,969,468 A | 11/1990 | Byers et al. | |
| 5,037,376 A | 8/1991 | Richmond et al. | |
| 5,040,533 A * | 8/1991 | Fearnot .................. | 607/22 |

(Continued)

FOREIGN PATENT DOCUMENTS

WO        WO 01/43635        6/2001

OTHER PUBLICATIONS

International Publication No. WO 03/035165, May 1, 2003, Nicolelis et al.

(Continued)

*Primary Examiner*—Kristen Droesch Mullen
(74) *Attorney, Agent, or Firm*—Finnegan, Henderson, Farabow, Garrett & Dunner, LLP

(57) ABSTRACT

According to embodiments of the invention, one or more implants in a body may be connected with optical fibers for transmitting data and/or power to or from the implants. Aspects of the invention related to various embodiments of the actual implant as well as to various embodiments for connecting optical fibers to the implants.

22 Claims, 16 Drawing Sheets

U.S. PATENT DOCUMENTS

| | | | |
|---|---|---|---|
| 5,081,990 A | 1/1992 | Deletis | |
| 5,119,832 A | 6/1992 | Xavier | |
| 5,156,844 A | 10/1992 | Aebischer et al. | |
| 5,215,088 A | 6/1993 | Normann et al. | |
| 5,325,865 A | 7/1994 | Beckman et al. | |
| 5,361,760 A | 11/1994 | Normann et al. | |
| 5,423,877 A | 6/1995 | Mackey | |
| 5,445,608 A | 8/1995 | Chen et al. | |
| 5,458,631 A | 10/1995 | Xavier | |
| 5,474,547 A | 12/1995 | Aebischer et al. | |
| 5,520,190 A * | 5/1996 | Benedict et al. | 600/513 |
| 5,617,871 A | 4/1997 | Burrows | |
| 5,638,826 A | 6/1997 | Wolpaw et al. | |
| 5,687,291 A | 11/1997 | Smyth | |
| 5,692,517 A | 12/1997 | Junker | |
| 5,697,951 A | 12/1997 | Harpstead et al. | |
| 5,702,432 A | 12/1997 | Chen et al. | |
| 5,713,923 A | 2/1998 | Ward et al. | |
| 5,735,885 A | 4/1998 | Howard, III et al. | |
| 5,758,651 A | 6/1998 | Nygard et al. | |
| 5,797,898 A | 8/1998 | Santini, Jr. et al. | |
| 5,814,089 A | 9/1998 | Stokes et al. | |
| 5,843,093 A | 12/1998 | Howard, III | |
| 5,843,142 A | 12/1998 | Sultan | |
| 5,855,801 A | 1/1999 | Lin et al. | |
| 5,873,368 A | 2/1999 | Sabin | |
| 5,873,840 A | 2/1999 | Neff | |
| 5,902,326 A * | 5/1999 | Lessar et al. | 607/36 |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |
| 6,001,065 A | 12/1999 | DeVito | |
| 6,006,124 A | 12/1999 | Fischell et al. | |
| 6,016,449 A | 1/2000 | Fischell et al. | |
| 6,024,700 A | 2/2000 | Nemirovski et al. | |
| 6,024,702 A | 2/2000 | Iversen | |
| 6,027,456 A | 2/2000 | Feler et al. | |
| 6,038,477 A | 3/2000 | Kayyali | |
| 6,061,593 A | 5/2000 | Fischell et al. | |
| 6,086,582 A | 7/2000 | Altman et al. | |
| 6,091,015 A | 7/2000 | del Valle et al. | |
| 6,092,058 A | 7/2000 | Smyth | |
| 6,113,553 A | 9/2000 | Chubbuck | |
| 6,125,300 A | 9/2000 | Weijand et al. | |
| 6,128,538 A | 10/2000 | Fischell et al. | |
| 6,134,474 A | 10/2000 | Fischell et al. | |
| 6,154,678 A | 11/2000 | Lauro | |
| 6,161,045 A | 12/2000 | Fischell et al. | |
| 6,163,725 A | 12/2000 | Peckham et al. | |
| 6,169,981 B1 | 1/2001 | Werbos | |
| 6,171,239 B1 | 1/2001 | Humphrey | |
| 6,175,762 B1 | 1/2001 | Kirkup et al. | |
| 6,181,965 B1 | 1/2001 | Loeb et al. | |
| 6,185,455 B1 | 2/2001 | Loeb et al. | |
| 6,216,045 B1 | 4/2001 | Black et al. | |
| 6,224,549 B1 | 5/2001 | Drongelen | |
| 6,240,315 B1 | 5/2001 | Mo et al. | |
| 6,254,536 B1 | 7/2001 | DeVito | |
| 6,263,237 B1 | 7/2001 | Rise | |
| 6,280,394 B1 | 8/2001 | Maloney et al. | |
| 6,309,410 B1 | 10/2001 | Kuzma et al. | |
| 6,313,093 B1 | 11/2001 | Frey, II | |
| 6,319,241 B1 | 11/2001 | King et al. | |
| 6,353,754 B1 | 3/2002 | Fischell et al. | |
| 6,354,299 B1 | 3/2002 | Fischell et al. | |
| 6,356,784 B1 | 3/2002 | Lozano et al. | |
| 6,358,202 B1 | 3/2002 | Arent | |
| 6,360,122 B1 | 3/2002 | Fischell et al. | |
| 6,427,086 B1 | 7/2002 | Fischell et al. | |
| 6,436,708 B1 | 8/2002 | Leone et al. | |
| 6,459,936 B2 | 10/2002 | Fischell et al. | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,620,415 B2 | 9/2003 | Donovan | |
| 6,702,847 B2 * | 3/2004 | DiCarlo | 623/1.34 |
| 6,711,440 B2 * | 3/2004 | Deal et al. | 607/9 |
| 7,076,292 B2 * | 7/2006 | Forsberg | 607/2 |
| 2001/0023368 A1 | 9/2001 | Black et al. | |
| 2001/0027336 A1 | 10/2001 | Gielen et al. | |
| 2001/0029391 A1 | 10/2001 | Gluckman et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0013612 A1 | 1/2002 | Whitehurst | |
| 2002/0016638 A1 | 2/2002 | Mitra et al. | |
| 2002/0077620 A1 | 6/2002 | Sweeney et al. | |
| 2002/0099412 A1 | 7/2002 | Fischell et al. | |
| 2002/0169485 A1 | 11/2002 | Pless et al. | |
| 2003/0082507 A1 | 5/2003 | Stypulkowski | |
| 2003/0083716 A1 | 5/2003 | Nicolelis et al. | |
| 2003/0093129 A1 | 5/2003 | Nicolelis et al. | |

OTHER PUBLICATIONS

International Publication No. WO 03/037231, May 8, 2003, Nicolelis et al.

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhorn et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2 , Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral Posterior Medial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minnesota Epilepsy Group of United and St. Paul Children's Hospital; and Human Motor Control Section, National Institute of Neurological Disorders and Stroke, National Institutes of Health, Electroencephalography and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. 1/2, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D. M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "Integrating assistive technologies: current practices and future possibilities," Med. Eng. Phys., vol. 18, No. 3, 1996, pp. 193-202.

Miguel A. L. Nicolelis et al., "Reconstructing the Engram: Simultaneous, Multisite, Many Single Neuron Recordings," Neuron,.vol. 18, Apr. 1997, pp. 529-537.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory systems," Proc. Natl. Acad. Science USA, vol. 94, Aug. 1997, pp. 9428-9433.

Nicolelis, Miguel A.L., "Trigeminal System Plasticity During Facial Anesthesia," Department of Health and Human Services, Public Health Service, Grant No. 2 R01 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al., "Premotor and Parietal Cortex: Cortiococortical Connectivity and Combinatorial Computations," Annual Review of Neuroscience, vol. 20, 1997, pp. 25-42.

P. R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Nicolelis, Miguel A.L., "Trigeminal System Plasticity During Facial Anethesia," Department of Health and Human Services, Public Health Service, Grant No. 2 R01 DE11451-06, Apr. 1999.

Gregor Rainer et al., "Prospective Coding for Objects in Primate Prefrontal Cortex," The Journal of Neuroscience, vol. 19, No. 13, Jul. 1, 1999, pp. 5493-5505.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.

E. M. Maynard et al., "Neuronal Interactions Improve Cortical Population Coding of Movement Direction," The Journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in Humans," The Journal of Neuroscience, vol. 20, No. 6, Mar. 15, 2000, pp. 2307-2314.

D. Gareth Evans et al., "Controlling Mouse Pointer Position Using an Infrared Head-Operated Joystick," IEEE Transactions on Rehabilitation Engineering, vol. 8, No. 1, Mar. 2000, pp. 107-117.

Qing Bai et al., "A High-Yield Microassembly Structure For Three-Dimensional Microelectrode Arrays," IEEE Transactions on Biomedical Engineering, vol. 47, No. 3, Mar. 2000, pp. 281-289.

Nicolelis, Miguel A.L., "Trigeminal System Plasticity During Facial Anethesia," Department of Health and Human Services, Public Health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of Health, Grant No. 1, R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related Potentials," IEEE Transactions on Rehabilitation Engineering, vol. 8, No. 2, Jun. 2000, pp. 180-185.

Robert E. Isaacs et al., "Work Toward Real-Time Control of a Cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prostheses for Restoration of Sensory and Motor Function," CRC Press, LLC, 2001, Chapters 6, 8 and 9, pp. 179-219, pp. 235-261, pp. 263-283.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public Health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," In Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Miguel A. L. Nicolelis, "Brain-machine interfaces to restore motor function and probe neural circuits," Nature Reviews, Neuroscience, vol. 4, May 2003, pp. 417-422.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter," Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, Issue 2, Oct. 13, 2003, pp. 1-16.

* cited by examiner

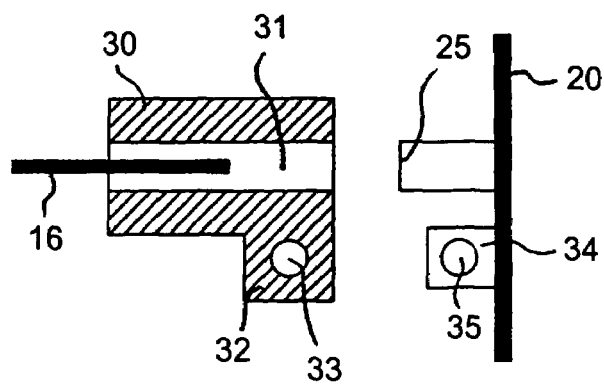
Figure 2C
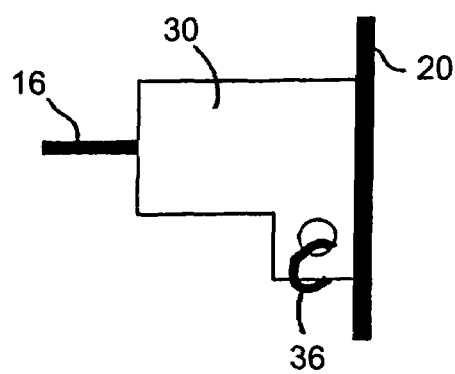
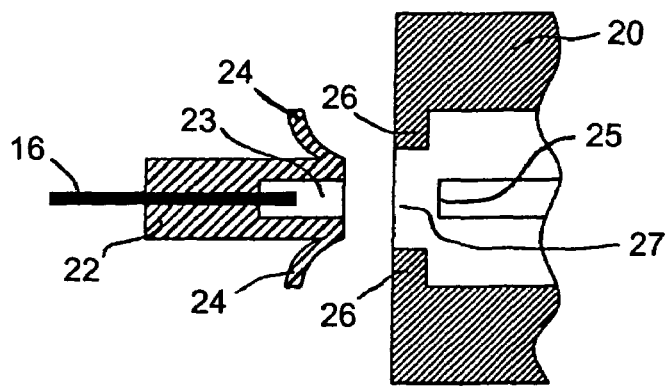
Figure 2B
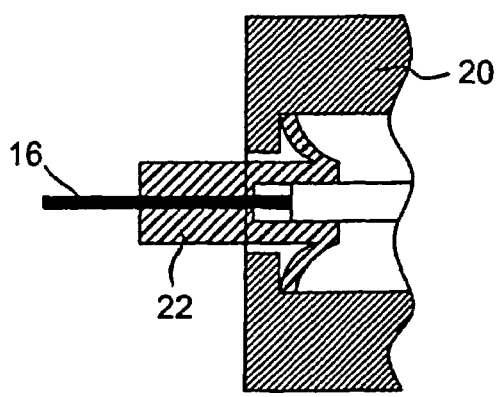

OPTICALLY-CONNECTED IMPLANTS AND RELATED SYSTEMS AND METHODS OF USE

RELATED APPLICATIONS

This patent application claims the benefits of priority of U.S. Provisional Application No. 60/385,761, filed Jun. 4, 2002, the entire contents of which are incorporated herein by reference.

GOVERNMENT SUPPORT

The U.S. Government may have certain rights in this invention as provided for by the terms of grant No. MDA972-00-1-0026 from the Defense Advanced Projects Agency.

DESCRIPTION OF THE INVENTION

1. Field of the Invention

The present invention relates to optical implants and associated systems and methods for using such implants in a body. More particularly, the invention relates to optically connected implant devices and associated methods and systems for communicating information to and from such implants.

2. Background of the Invention

Recent advances in neurophysiology have allowed researchers to study the electrical activity of highly localized groups of neurons with high temporal accuracy and in specific locations in the brain. These advances create the possibility for brain-computer interfaces allowing an amputee to control a prosthetic limb in much the same way that the amputee would control a natural limb. Although noninvasive sensors, such as multichannel electroencephalogram (EEG) sensors placed on the surface of a person's skin, have been used as simple brain-computer interfaces, they do not currently offer the temporal or spatial resolution needed for prosthetic control. Such noninvasive sensors can detect only mass fluctuations of neuron activity that have been attenuated by the intervening bone and tissue. As a result, these types of brain-computer interfaces can derive only simple forms of information from the neuron activity. They also operate very slowly because the mass neuron signal activity only modulates at very low rates, requiring more processing time.

More advanced brain-computer interfaces use sensing electrodes placed directly in contact with the brain to detect neuron activity. These electrodes, which may comprise a micro-wire or hatpin-like electrode, each form a recording channel that directly detects the electrical impulse signal from all of the neurons in the electrode's vicinity. Further signal processing then isolates the individual neuron signals, each of which comprises a series of electrical spikes reflecting information correlated to a respective function (e.g., a particular movement of a particular limb). The brain encodes this information according to the frequency or firing rate of the spikes. By collecting the firing rates of a number of individual neuron signals detected via a number of recording channels, a brain-computer interface can derive control signals to control a neural prosthetic device.

Many types of therapeutic devices, including brain-computer interfaces, can be implanted into the body, such as muscle stimulators, magnetic therapy devices, or drug delivery systems. A number of such devices may also be implanted where the different implants may then communicate with one another. In such cases, using electronic wiring to connect the interfaces to one another has a number of drawbacks. For one, the electrical wiring may corrode upon being exposed to bodily fluids. Electrical wires also act as antennas and are thus susceptible to picking up undesirable electronic noise, which may have a significant impact on the low amplitude data signals communicated in an implant system. Further, transmitting electrical signals through the body presents a number of issues associated with insulating the person from electrical shock. Moreover, systems using traditional electrical wiring for communicating power and data require a substantial amount of energy to power the system. For an implanted system that runs continuously, a more energy efficient solution is needed.

Therefore, an implant system is desired in which power, data, and other information may be communicated in ways solving the above issues.

SUMMARY OF THE INVENTION

According to a first aspect of the invention, a system for treating a body is disclosed. The system comprises a first device configured to be implanted within the body and a second device. An optical fiber, optically connected to the first device and the second device, is configured to be at least partially implanted in the body and capable of transmitting power and data between the first device and the second device.

According to a second aspect of the invention, a system for treating a body is disclosed. The system comprises a first device configured to be implanted within the body and a second device. An optical fiber, optically connected to the first device and the second device, is configured to be at least partially implanted in the body and capable of transmitting data between the first device and the second device. An electrical conductor is connected to the first device and the second device. The electrical conductor is configured to be at least partially implanted in the body and is capable of transmitting electrical power between the first device and the second device.

According to a third aspect of the invention, a system for treating a body is disclosed. The system comprises a first device configured to be implanted within the body. The first device includes a photoreceiver capable of receiving light. A second device is configured to be implanted within the body. An optical fiber is optically connected to the first device and the second device, and is configured to be implanted in the body and capable of transmitting light from the first device to the second device.

According to a fourth aspect of the invention, a system for treating a body is disclosed. The system comprises a first device configured to be implanted within the body, an encapsulation covering substantially all of the first device to seal the first device from bodily fluids, and an optical window associated with the first device and not covered by the encapsulation.

According to a fifth aspect of the invention, a system for detecting neural signals from a brain of a body is disclosed. The system comprises a device sized and configured for implantation proximate the brain. The device includes an array of electrodes capable of sensing neural signals and at least one first optical fiber coupled to the device and capable of providing an optical communication with the device.

According to a sixth aspect of the invention, a method for treating a body is disclosed. The method comprises: implanting a first device in the body, implanting at least a portion of an optical fiber in the body, optically connecting the first device to a first end of the optical fiber, optically connecting a second device to a second end of the optical fiber, transmitting power and data between the first device and the second device, and using the power and data to perform a therapeutic function for the body.

According to a seventh aspect of the invention, a method for treating a body is disclosed. The method comprises: implanting a first device in the body, implanting at least a portion of an optical fiber in the body, implanting at least a portion of an electrical conductor in the body, optically connecting the first device to a first end of the optical fiber, optically connecting a second device to a second end of the optical fiber, electrically connecting the first device to a first end of the electrical conductor, electrically connecting the second device to a second end of the electrical conductor, transmitting data along the optical fiber between the first device and the second device, transmitting power along the electrical conductor between the first device and the second device, and using the power and data to perform a therapeutic function for the body.

According to an eighth aspect of the invention, a method for treating a body is disclosed. The method comprises: implanting in the body a first device having a photoreceiver, implanting a second device in the body, implanting an optical fiber in the body, optically connecting the first device to a first end of the optical fiber, optically connecting the second device to a second end of the optical fiber, transmitting light along the optical fiber between the first device and the second device, and using the light to perform a therapeutic function for the body.

According to a ninth aspect of the invention, a method for treating a body is disclosed. The method comprises: implanting in the body a first device having an encapsulation covering substantially all of the first device to seal it from bodily fluids and having an optical window not covered by the encapsulation, implanting at least a portion of an optical fiber in the body, optically coupling the optical window to a first end of the optical fiber, optically connecting a second device to a second end of the optical fiber, transmitting at least one of light, power, and data along the optical fiber between the first device and the second device, and using the at least one of light, power, and data to perform a therapeutic function for the body.

According to a tenth aspect of the invention, a method for detecting neural signals from a brain of a body is disclosed. The method comprises: providing a device that includes an array of electrodes, implanting the device proximate the brain, implanting at least a portion of a first optical fiber in the body, optically coupling a first end of the first optical fiber to the device, and sensing neural signals with the array of electrodes.

Both the foregoing general description and the following detailed description are exemplary and are intended to provide further explanation of the embodiments of the invention as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIGS. 2A-2C illustrate various connectors for coupling an optical fiber 16 and an implant housing 20, according to an exemplary embodiment consistent with the present invention;

FIG. 3F illustrates a structure of a power splitter consistent with an exemplary embodiment of the present invention, while

DESCRIPTION OF THE EMBODIMENTS

Figure 1:
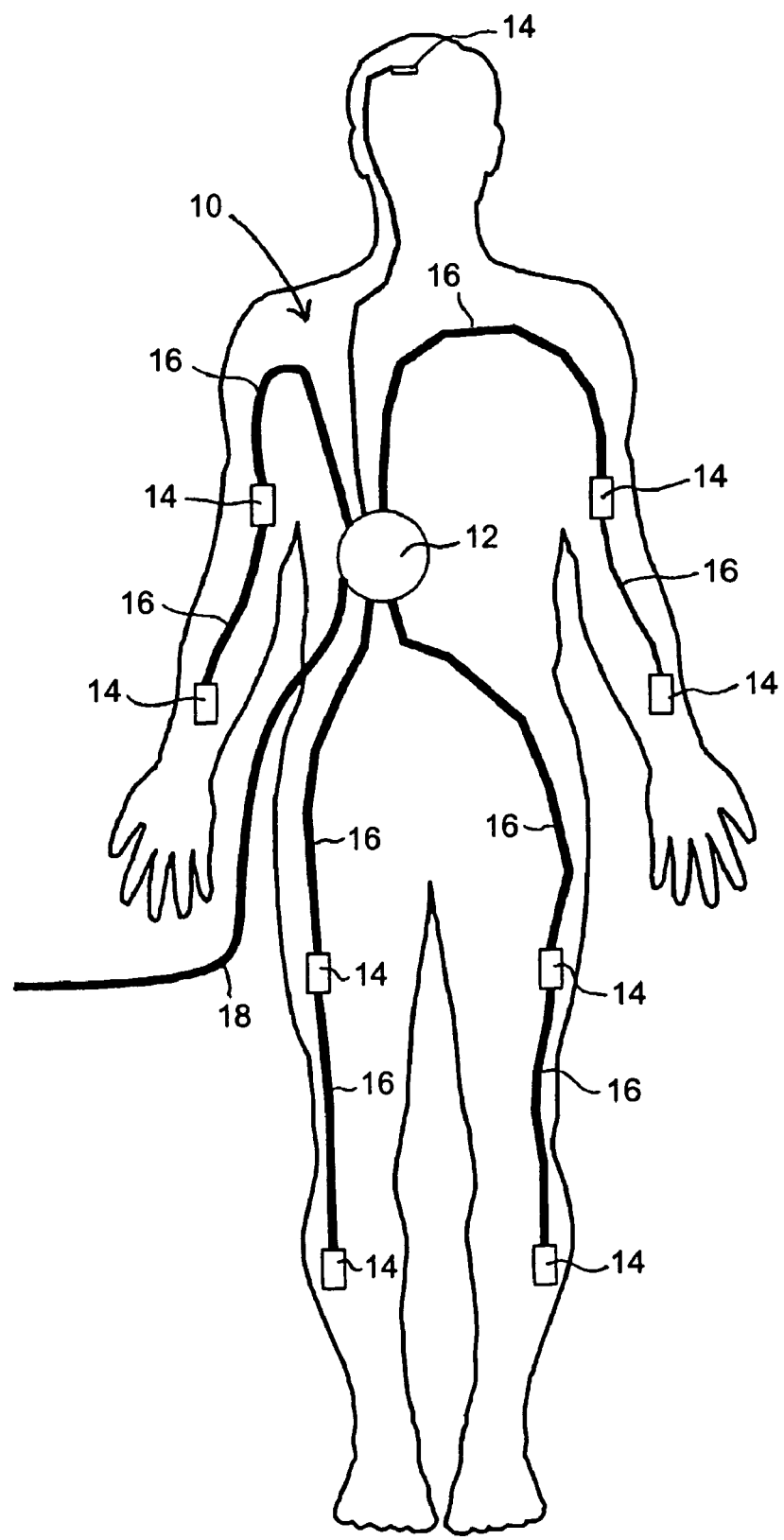
FIG. 1 shows a system 10 of implants and optical fibers implanted in a body 12, according to an exemplary embodiment consistent with the present invention.

Reference will now be made in detail to the present embodiments of the invention, examples of which are illustrated in the accompanying drawings. Wherever possible, the same reference numbers will be used throughout the drawings to refer to the same or like parts.

According to embodiments of the invention, one or more implants in a body may be connected with optical fibers for transmitting data and/or power to or from the implants. Connecting implants with optical fibers has numerous benefits, including, for example, avoiding the antenna effect caused by conventional electrical conductors. This is especially beneficial in when transmitting low amplitude signal data, as may be done when transmitting to devices implanted in the human body. Further, in comparison to conventional electrical conductors, optical fiber connections have improved long-term material compatibility and durability and permit simplified two-way communication.

The optical fibers can be contained within the body and used to connect two or more implants. In addition, or alternatively, one or more optical fibers can enter a body transcutaneously to connect one or more implants to a module or device outside of the body. A system with multiple implants, as opposed to one implant having all the desired functionality, permits smaller implants that may be placed in tight spaces or locations within the body, such as the brain, and locations less accessible to light penetration.

A multiple implant system also permits smaller implants to connect to larger implants, where the larger implant may handle power supply, signal processing, or other functionality. This would thus allow the smaller implant to thus have a smaller size and, in turn, to be located in a desired particular area in the body. The larger implants may then be located in larger, more remote, volume areas within the body, such as the chest, abdomen, or thigh, for example.

In one embodiment, optical fibers can connect multiple implants in a chain configuration. Such an arrangement permits a less complicated implant procedure and minimizes or eliminates signal loss. As an alternative, multiple implants can be connected individually to a central implant that may include larger components providing, for example, a power supply. Implants that may be used in systems according to embodiments of the invention include, for example, electrode assemblies, stimulators for the brain, muscles, organs, heart, or other parts of a body, signal processing devices such as spike sorters, encoders, decoders, processing algorithms, or the like, drug delivery devices, power supplies such as batteries, capacitors, or the like, cardiac pacing devices, pain control devices, transcutaneous electrical nerve stimulations (TENS) devices for controlling pain, magnetic therapy devices, radiation delivery devices, or any other therapeutic or diagnostic device useful in treating the body. An electrode assembly implant may be placed on or in the brain or nerve, or any location proximal thereto. In many applications, implants are miniaturized and have low power consumption, low heat output, and a long life.

The one or more optical fibers can carry light representing a data stream, light to be converted to electrical or other energy (e.g., to power an implant), UV light for infection control, ultrasound, or other forms of energy compatible with optical fibers and useful for a particular system. For example, a single optical fiber can carry both power and data to or form an implant. A single optical fiber also can carry multiple wavelength light and/or can carry two-way communication signals. The type of data that the fibers may carry can include neural signal information.

The one or implants that connect to one or more optical fibers may include structure that may be used for, for example, a power source, data transmission, signal processing, telemetry to communicate with an external device, sensors (such as one or more electrode assemblies) for detecting signals or other data from a body, ultrasound data and/or power transmission, preventing or reducing infection within a body through the use of UV light, electrical stimulators, conversion of light to electrical power, or any other suitable function, including any therapeutic or diagnostic function in embodiments using implants within a body. A single implant may include structure for performing one or more of these functions. The electrical energy generated by an implant may be used, for example, to charge an electrical energy storage device, for example a battery or capacitor, of another implant.

In certain embodiments, it may be preferred that the first implant, i.e. the implant that communicates with an external device, includes a transcutaneous photoreceiver that then sends light to one or more separate implants in the body. The first implant also may include a transceiver for wirelessly communicating with one or more external devices. To best serve these purposes, the first implant may be placed close to the skin allowing it to receive light from a source external to the body, and also may be placed in an area of the body that can accommodate a relatively larger implant. The separate implants in communication with the first implant may be placed deeper in the body in places less accessible to penetrating light, such as under bone. The separate implants can include other functionality, such as signal processing, power source, sensors such as electrode assemblies, conversion of light to another form of energy (e.g., electrical energy or power), conversion of light energy to data, and/or use of UV light to prevent/reduce infection.

FIG. 1 shows a system 10 of implants and optical fibers implanted in a body, according to an exemplary embodiment of the invention. System 10 includes a central implant 12 placed within the abdomen and connected to various implants 14 arranged throughout the body, and particularly in the arms, legs, and brain of the body. Implants 14 in the limbs may receive, for example, control signals for controlling motion of the limbs, and implant 14 in the brain may include sensing electrodes placed directly in contact with the brain to detect neuron activity. As described above, signal processing, preferably associated with one or more of the implants 12 or 14, may derive the control signals used by implants 14 in the limbs.

Implants 12 and 14 are connected by optical fibers 16. As shown in FIG. 1, one fiber 16 extends to the implant 14 in the brain, and a fiber 16 extends to the implants 14 in each limb. The implants 14 in each limb are arranged in a chain configuration. In addition, system 10 includes a transcutaneous fiber 18 that can couple implant 12 to an external device.

Figure 4A:
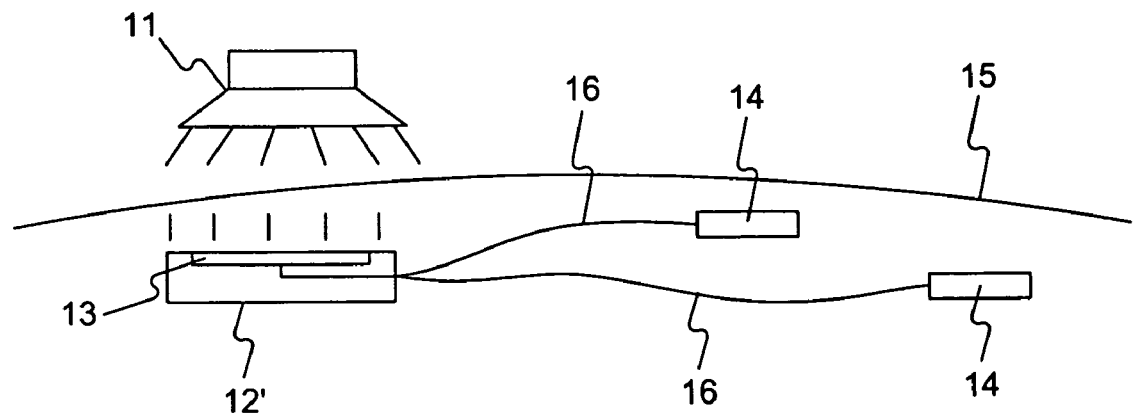
FIGS. 4A and 4B further illustrate an implant system interfacing with a light source according to exemplary embodiments consistent with the invention.
Figure 4B:
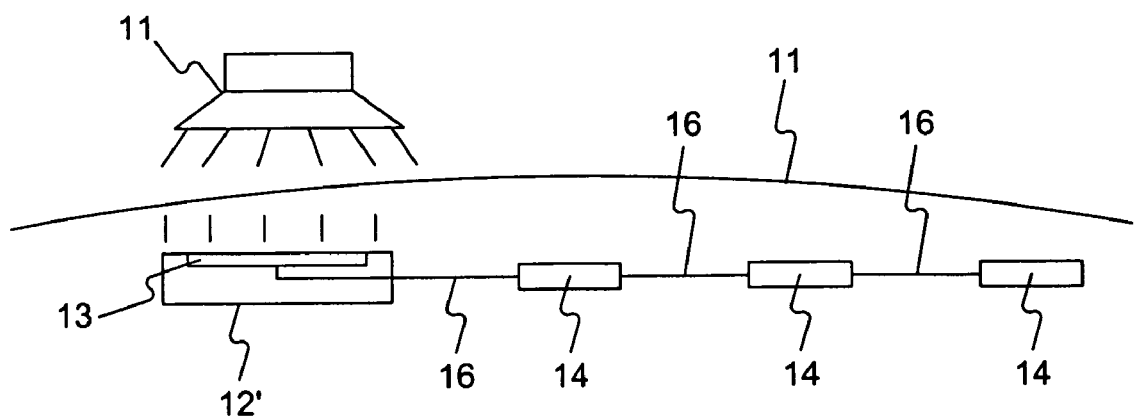

FIGS. 4A and 4B show additional details of a system of implants according to embodiments of the invention. In the system of FIG. 4A, a first, central implant 12' is implanted under the skin of a body 15. Implant 12' includes a photoreceiver 13 positioned to receive light form a light source 11 external to body 15. Light source 11 may be natural light (i.e. sunlight), other ambient light from sources near the body such as commercial lighting within a room, light from a UV source for infection control, an external light source connected to the body and powered by solar cells, batteries or other suitable power, or any other source of light capable of penetrating through skin. As an alternative, at least a portion of implant 12' may be transcutaneous or located external the body, such that a portion of photoreceiver 13 is located external to the skin, allowing, for example, implant 12' to then receive light directly. In either case, implant 12' receives light and sends light to one or more implants 14 arranged in a chain (FIG. 4B), parallel (FIG. 4A), or a combination of these arrangements. Implants 14 may perform any of the functions described above.

While FIGS. 4A and 4B illustrate powering an implant via a light source, implants may also be powered by an inductive coupling device, as well known in the art. In such as case, the implant may include an inductive coil. When an inductor external to the body under an applied AC voltage is placed in close proximity to the implant, an AC voltage is induced in the implant's coil. The induced voltage can then be used to power the implant.

Figure 6:
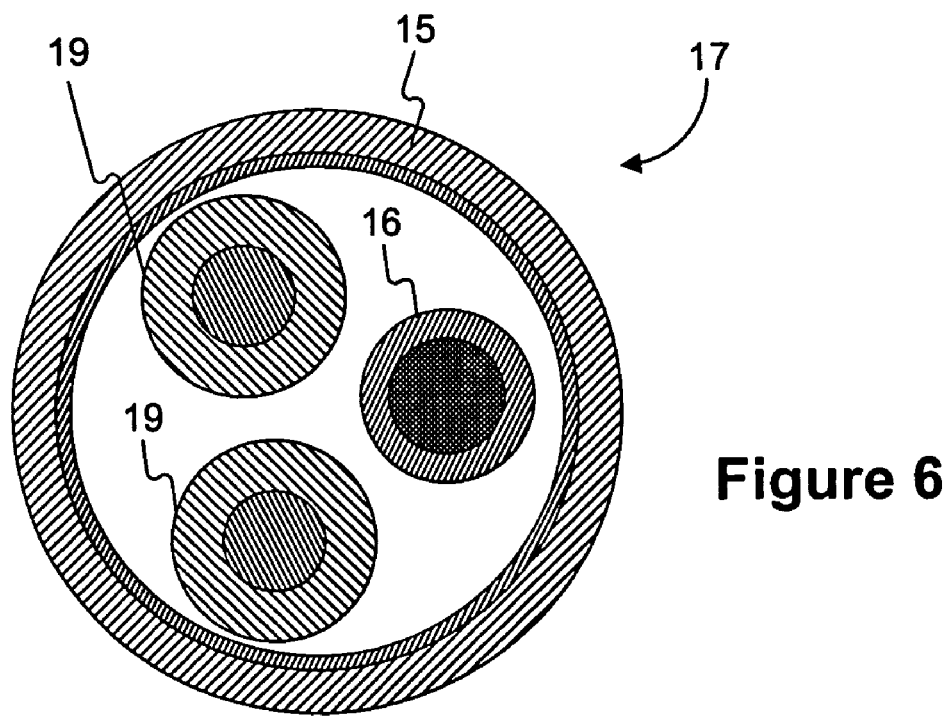
FIG. 6 shows an exemplary fiber optic cable according to an exemplary embodiment of the invention.

Further, as described above, optical fibers consistent with the present invention may be used to carry not only data, but other forms of energy (e.g., UV or ultrasound energy) for purposes other than conversion to electrical energy to power an implant. According to further embodiments of the invention, optical fibers may be used to carry data and other information to or from the implant, while electrical conductors (such as metal wires) may be used to carry electrical power to the implant. The optical fibers and electrical conductors may then run or track through the body separately, i.e. the two may be unbundled between the implants. Alternatively, one or more optical fibers may be combined with one or more electrical conductors in a cable-like configuration. In this respect, FIG. 6 shows an exemplary cable 17 according to an embodiment of the invention. As shown in FIG. 6, cable 17 includes an optical fiber 16 and two electrical conductors 19 arranged within a flexible jacket 15. Jacket 15 may have multiple shielding or insulating layers known to those skilled in the art. Further, optical fiber 16 may include an inner fiber surrounded by appropriate light reflective cladding material and potentially a protective jacket. Each electrical conductor 19 may include an inner wire surrounded by an insulator. Cable 17 may also include a grounding shield, for example, within jacket 15. Cables used in systems of the present invention may include any suitable number and type of optical fibers and electrical conductors desired for the intended purpose.

Implant systems employing cables having an optical fiber for communicating data and an electrical conductor for communicating power, may thus overcome many of the disadvantages associated with transmitting signals over electrical conductors. For example, by using optical fibers 16 as shown in FIG. 6, the data transmitted over the optical fibers are not susceptible to electrical interference from the electrical conductor 19 (e.g., via an "antenna effect"). Moreover, by using electrical conductors within the same cable, the invention allows for transmitting power more efficiently over the electrical conductor 19, where losses are not incurred due to a light to electrical energy conversion. Thus, the invention of FIG. 6 allows for transmitting a low noise data signal over optical fiber 16 while also transmitting an electrical power signal within the same cable at high transmission efficiencies.

A system of one or more implants, such as system 10 for example, can be pre-connected prior to implantation or may be connected intra-operatively (e.g., when being implanted within the body during surgery). The optical fibers (and/or cables or electrical conductors) may connect to one or more implants through any suitable method and structure. According to an aspect of the invention, all or substantially all of the implant may be sealed, i.e. be encapsulated, so that bodily fluids or other foreign matter does not enter the implant. Such a sealed implant may include an optical window for mating with the end of an optical fiber to transmit and/or receive data, information, energy, or the like.

Figure 2A:
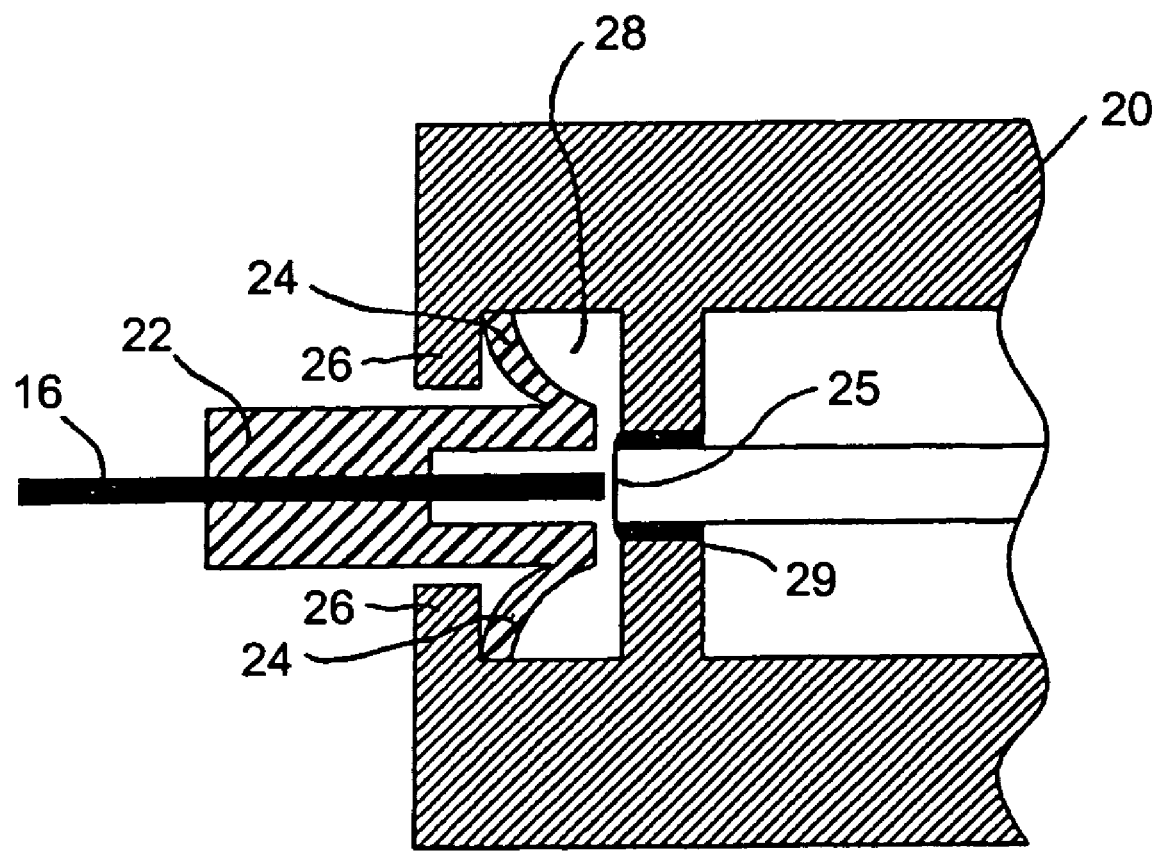

FIG. 2A shows a snap-fit connection between an optical fiber 16 and an implant housing 20, according to an exemplary embodiment of the invention. An end of fiber 16 includes a snap connector 22 with resilient flanges 24. Fiber 16 extends through and is centered within connector 22. Housing 20 includes extensions 26 that define an opening 27 (see FIG. 2B) that receives connector 22 into an area 28. The size of opening 27 and area 28 permit introduction of connector 22 so that its flanges 24 engage an interior side of extensions 26 and restrict connector 22 and its connected fiber 16 from exiting area 28.

Implant housing 20 also contains a transparent optic window 25 facing the end of fiber 16 to receive power, data, or other energy or information carried by fiber 16, or transmit energy or information to fiber 16. Window 25 may transmit the specific light used without requiring a pass through (i.e., a sealed opening between the implant's outside surface and its internal components that allows an electrical contact to be made to the internal components) or sealed exposed electrical contacts, both of which can cause contamination issues before, during, and after surgery. Window 25 may include a focusing lens, aperture, beam splitter, or other suitable optical components to aid in communicating data, information, or energy to or from fiber 16. Window 25 may connect to a port in housing 20 by any suitable sealing agent 29, such as glue, to fix window 25 in position relative to fiber 16.

Other embodiments of a snap-fit connection may have optic window 25 free standing and not sealed within a port, as shown in FIG. 2B. In this embodiment, the end of fiber 16 is recessed within the a receiving hole 23 at the distal end of connector 22. Hole 23 receives optic window 25 to mate window 25 with fiber 16, as shown in the bottom schematic of FIG. 2B. The snap fit connections shown in FIGS. 2A and 2B may be especially convenient for simple attachment during surgery.

Other structure and techniques for connecting one or more optical fibers to one or more implants may be used. For example, systems according to embodiments of the invention may use a suture-tab connection, as shown in FIG. 2C. According to this embodiment, fiber 16 is received within a passage 31 of a suture lock connector 30. Connector 30 also includes a suture tab 32 defining a hole 33. An optic window 25 and a suture tab 34 extend from an exterior surface of implant housing 20. Optic window 25 is received within passage 31 to mate window 25 with fiber 16. Tab 34 is received within tab 32 of connector 30 to align a hole 35 of tab 34 with hole 33. As shown in the bottom drawing of FIG. 2C, a suture 36 then may be placed intra-operatively within aligned holes 33 and 35 to secure the connection.

Still other structures and techniques for connecting optical fibers with implants maybe used in connection with systems of the invention. Those structures and techniques include screw-on connection with threaded connectors, pressure (friction) fit connectors, captured flange (i.e. bayonet lock) connectors, connectors that permanently attach, connectors that are detachable, or connectors that may have safety features allowing them to be more easily attached than detached (e.g. child-proof pill bottle thread configurations). The disclosed connections permit implants that are simpler to manufacture and do not require sealing during the surgical procedure, minimizing surgery time and risk to the patient.

Further, the implant itself may be sealed during a manufacturing stage to protect it from bodily fluids after being implanted. For example, the complete implant assembly may be dipped in or sprayed with a sealing material, or seams may be welded, glued, or otherwise sealed. These various sealing methods may be thus be used to seal any openings of the implant and to insulate any of the implant's electrical contacts. As part of the manufacturing process, the implant can be tested for leaks or its seal integrity prior to packaging.

Figure 3A:
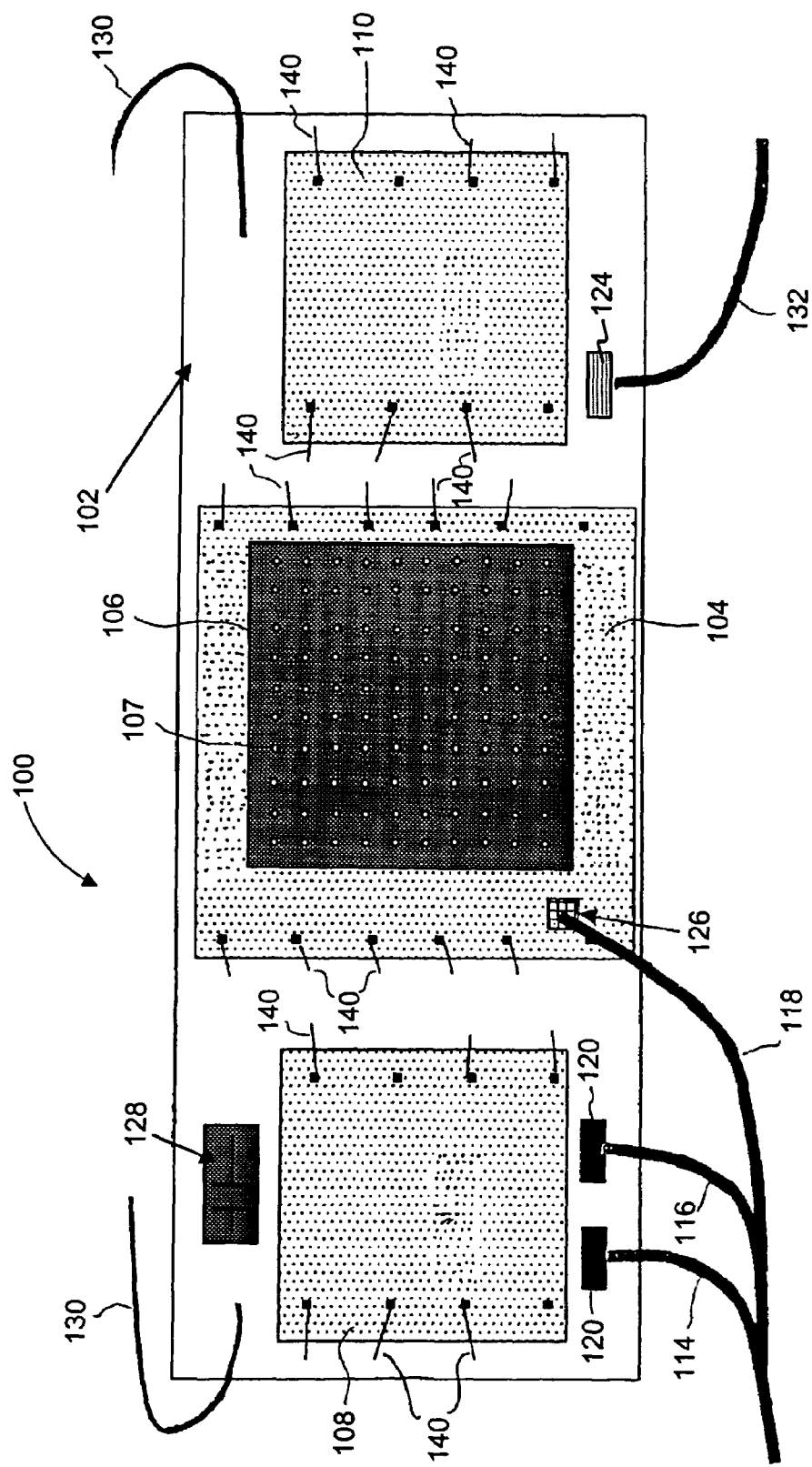
FIGS. 3A and 3B illustrate an implant system 100 according to an exemplary embodiment consistent with the present invention.
Figure 3B:
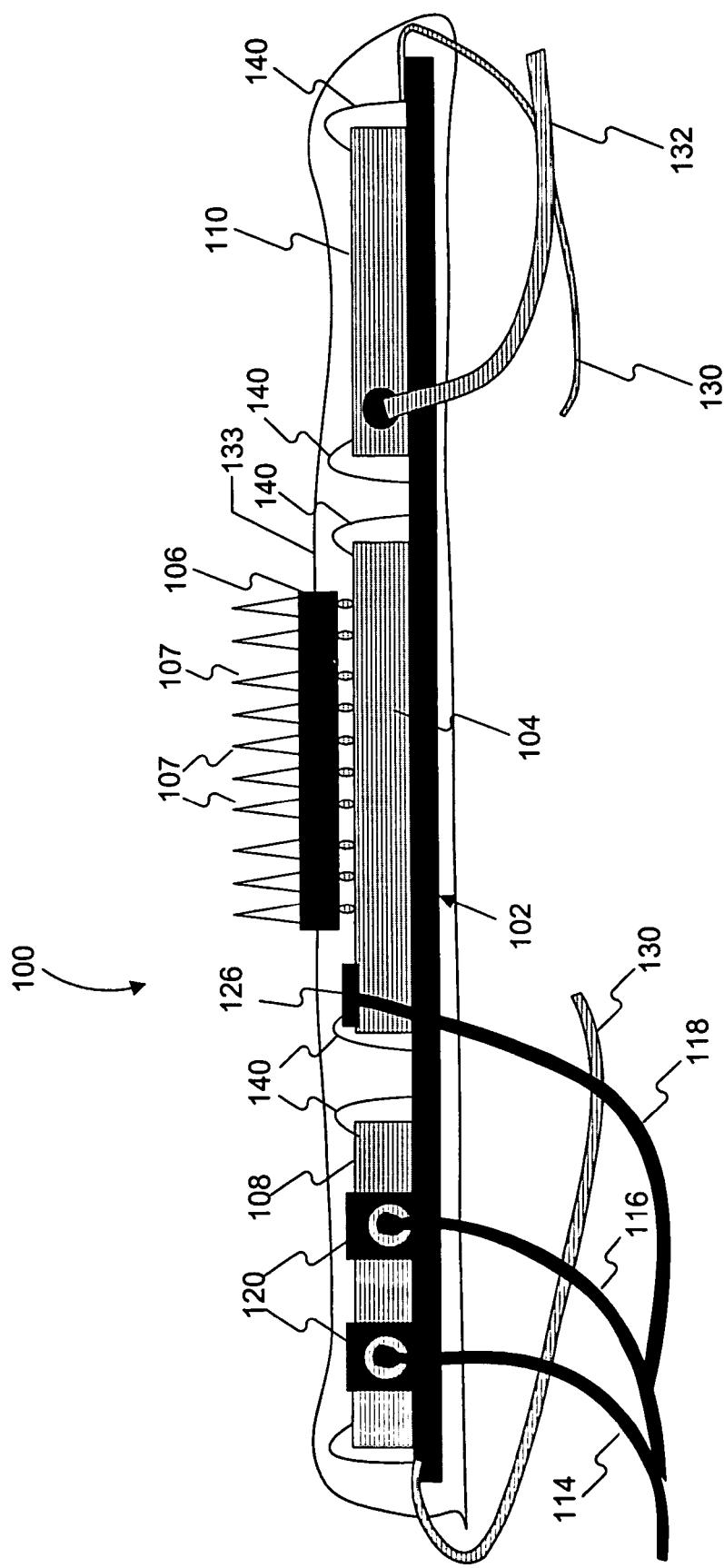

FIGS. 3A and 3B show an implantable system 100 according to an embodiment of the invention particularly suited for measuring motor cortex activity in primates. System 100 is a combined array and signal processor with a fabricated custom integrated circuit (IC) having optical fiber input and output. System 100 includes a substrate 102 upon which a number of components are mounted and interconnected. Those components include a chip 104, an array 106 of probes 107, analog-to-digital converters 108 and 110, photodiodes 120, an LED 124, a clock photodiode 126, and a bypass capacitor 128. Reference electrodes 130 connect to and extend from substrate 102. Optical fibers 114, 116, and 118 provide power and clock input to system 100 and optical fiber 132 carries return signals from system 100. These components and their interconnection will now be described in more detail.

Substrate 102 may be made of $Al_2O_3$, GaAs, polyamide, or any other biocompatible material known in art that is suitable for implantation, mounting of components, and optical and electrical interconnection of those components. Substrate 102 may have a size of approximately 1.9 cm by 0.7 cm. With the components assembled onto substrate 102, assembly 100 may then have a depth of approximately 2.4 mm. Substrate 102 and the remainder of assembly 100 may be encapsulated by a suitable dielectric material 133, as shown in FIG. 3B. Encapsulation material 133 seals all components together, with probes 107, optical fibers 114, 116, 118, and 132, and reference electrodes 130 extending from encapsulation 133.

Array 106 may be a 10×10 of neural probes 107. Each neural probe 107 may comprise an electrode for detecting electrical brain signals or impulses. Array 106 may be placed in any location of a patient's brain allowing for array 106 to detect electrical brain signals or impulses. Electrode array 110 serves as the sensor for the brain implant system. While the Figures illustrate array 106 as having one hundred probes 107 arranged in an 10×10 matrix, array 106 may include one or more probes having a variety of sizes, lengths, shapes, forms, and arrangements. Each probe 107 extends into the brain to detect the electrical neural signals generated from the neurons located in proximity to the electrode's placement within the brain. Neurons may generate such signals when, for example, the brain instructs a particular limb to move in a particular way.

U.S. patent application Ser. No. 10/278,853 to Donoghue et al. and entitled "Microstructured Arrays for Cortex Interaction and Related Methods of Manufacture and Use" discloses arrays of probes and methods of their manufacture suitable for use in connection with systems according to embodiments of this invention. The entire disclosure of that patent application is incorporated by reference herein. In addition, U.S. Pat. No. 6,171,239 to Humphrey and entitled "Systems, Methods, and Devices for Controlling External Devices By Signals Derived Directly From the Nervous System" and U.S. Pat. No. 5,215,088 to Normann et al. and entitled "Three-Dimensional Electrode Device" each disclose other arrays suitable for use in connection with systems according to embodiments of this invention. The entire disclosures of those patents are also incorporated by reference herein. Other arrays of probes capable of detecting electrical neural signals generated from the neurons may be used with systems according to embodiments of the invention.

Figure 3C:
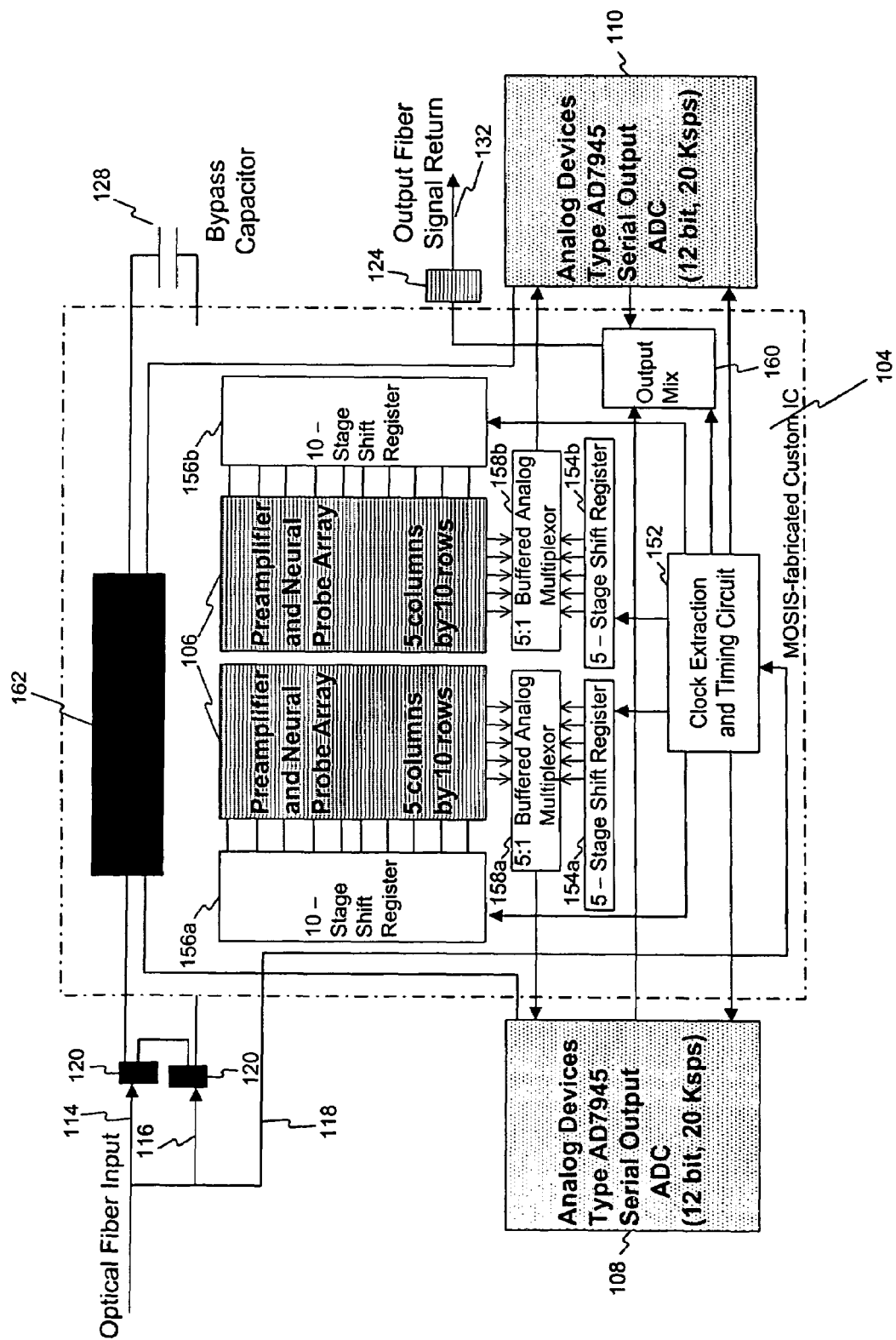
FIG. 3C is a block diagram showing, in one exemplary embodiment consistent with the present invention, the circuit components of implant system 100.

Chip 104 preferably is a fabricated custom IC. FIG. 3C is a block diagram showing, in one exemplary embodiment, the components of chip 104 and their interconnection. As shown in FIG. 3C, chip 104 may further include a clock extraction and timing circuit 152, 5-stage shift registers 154a and 154b, 10-stage shift registers 156a and 156b, 5:1 buffered analog multiplexors 158a and 158b, an output multiplexor 160, and a voltage regulator 162.

Clock extraction circuit 152 receives a clock signal over fiber optic cable 118 and extracts a clock signal for controlling the timing of the various components included on chip 104, including shift registers 156 and 158, converters 108, 110, and multiplexor 160. For instance, under the control of the extracted clock signal, shift registers 156 may sequentially shift the input data detected by a row of probes 107 of array 106 to analog multiplexors 158. Thus, in the exemplary embodiment, each shift register 156 first shifts the data from the five probe inputs of the first row, then shifts the data from the five probe inputs of the second row, and so forth. Analog multiplexors 158 may then multiplex the five received input signals into a multiplexed analog output stream for input to analog-to-digital converters 108, 110. Further, as shown in FIG. 3C, shift registers 154 may be used to control the clocking of multiplexors 158 based on the clock signal received from extraction circuit 152.

Analog-to-digital converters 108, 110 may be any suitable low power analog-to digital (A/D) converter. In one exemplary embodiment, A/D converters 108, 110 may be implemented by using a 12 bit, 20 Kbs A/D converter. Converters 108, 110 electrically connect to substrate 102 through a plurality of lead wires 140 bonded to converters 108, 110. Converters 108, 110 receive the multiplexed analog data from multiplexors 158 and digitize the analog signals. Converters 108, 110 then send the digitized data to output multiplexor 160, which multiplexes the two digital data streams from converters 108, 110 for outputting to output optical fiber 132 via LED 124.

Further, as shown in FIG. 3C, voltage regulator 162 receives a power signal from optical fiber 114 via photodiodes 120. Based on the input power signal, regulator 162 then outputs a voltage power supply signal for powering the components of chip 104. For instance, as shown in FIG. 3C, regulator 162 provides a power supply to converters 108, 110.

Referring to FIGS. 3A and 3C, LED 124 of system 100 may be any known in the art that is suitable for receiving an electrical signal and providing that signal to an optical fiber. In the embodiment shown, LED 124 receives a signal from output multiplexor 160 and provides an output return signal to optical fiber 132.

Clock photodiode 126 may be mounted directly to chip 104 and receive an optical input from optical fiber 118. Fiber 118 may branch from a single optical fiber that also branches to fibers 114 and 116 or may be an entirely separate fiber that individually communicates with an optical source. Fiber 118 provides a clock input to photodiode 126 that connects to clock extraction and timing circuit 152 of chip 104.

A bypass capacitor 128 connects to voltage regulator 162. Capacitor 128 may, for example, provide fault protection, such as protection against an electrical short. Reference electrodes 130 connect to and extend from substrate 102. Electrodes 130 may make electrical contact with the surrounding tissue of the body in which the system 100 is implanted and thus provide a voltage reference point or "ground" for chip 104.

Figure 3D:
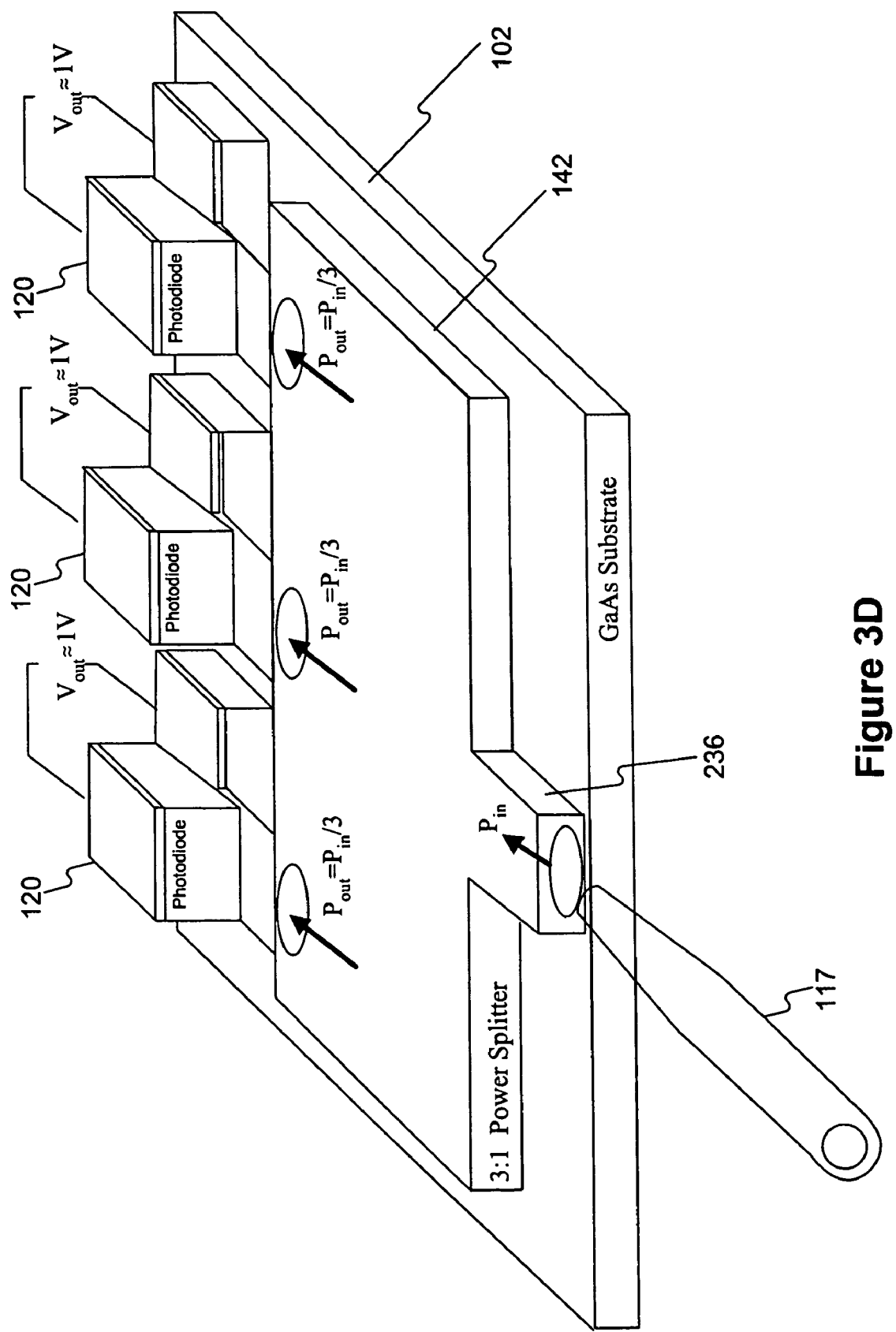
FIG. 3D shows an exemplary arrangement, consistent with the present invention, for coupling a fiber optic cable to multiple photodiodes via a power splitter.

As described above, photodiodes 120 mount to substrate 102 and receive optical power input from optical fibers 114, 116. Two photodiodes are shown in the embodiment shown in FIGS. 3A-3C. However, any number and type of photodiodes suitable for converting optical power to an electrical voltage may be used in a system according to embodiments of the invention. For example, FIG. 3D shows the use of three photodiodes 120 receiving optical power from a power splitter 142 also mounted to substrate 102. In an embodiment, photodiodes 120 are interconnected, as shown in FIG. 3C, and send output to voltage regulator 162.

Figure 3E:
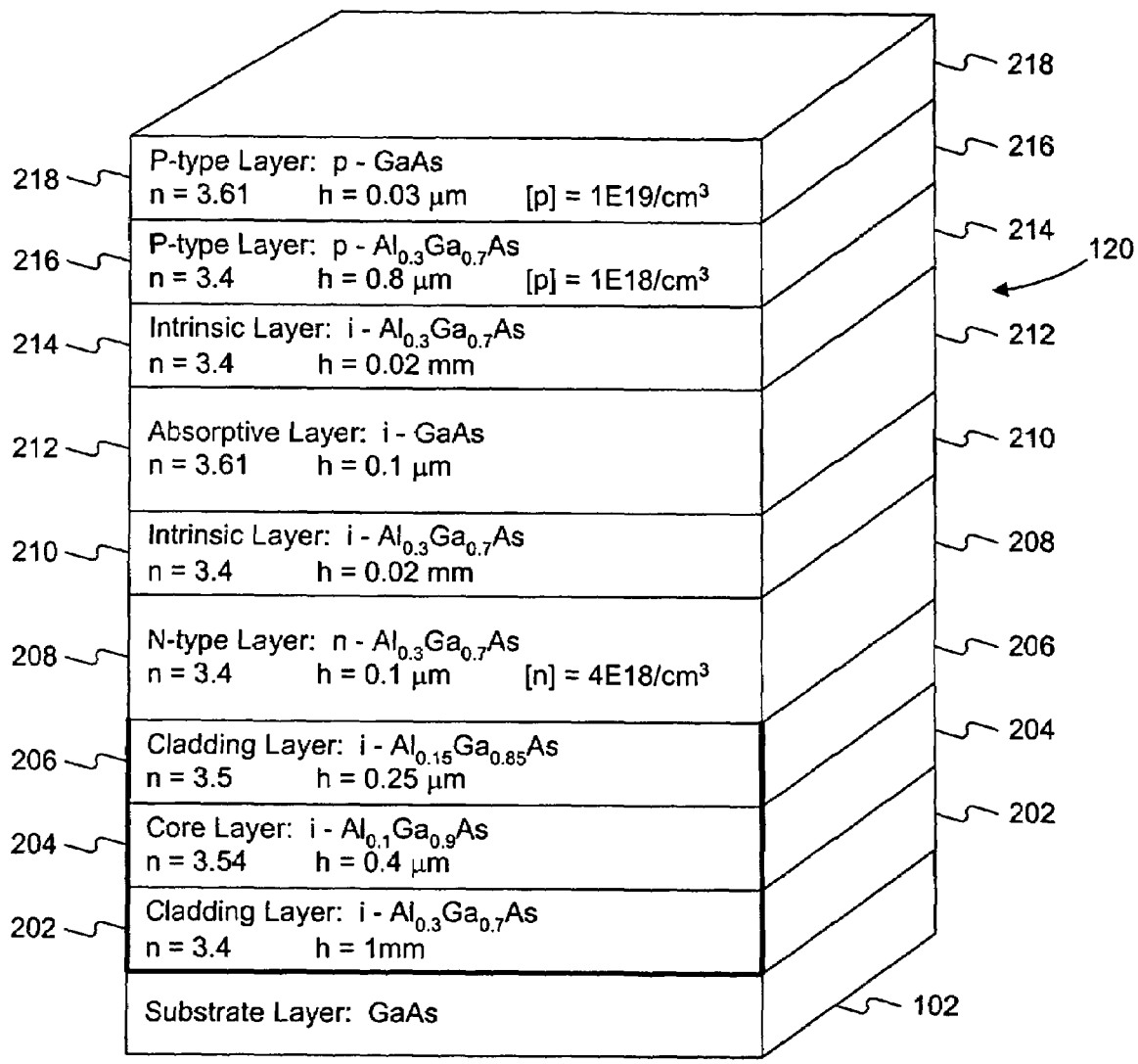
FIG. 3E illustrates a structure of a photodiode consistent with an exemplary embodiment of the present invention.
Figure 3G:
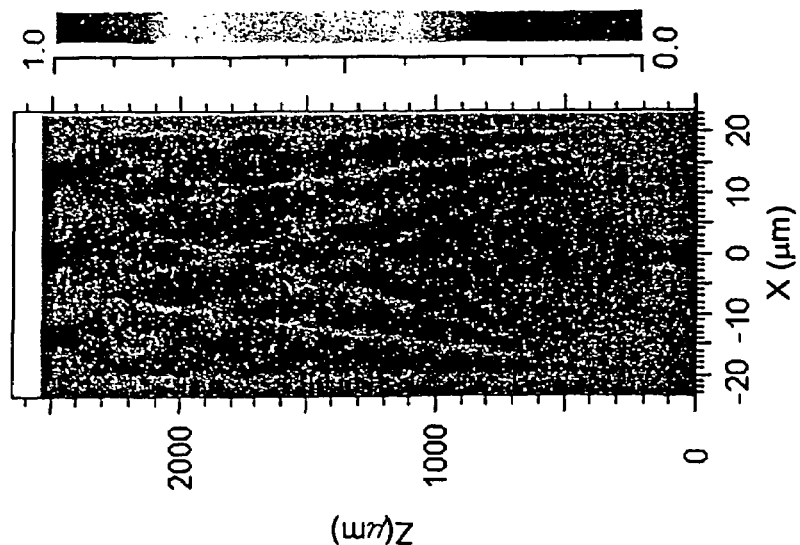
FIG. 3G illustrates the optical splitting detail of the power splitter.
Figure 3F:
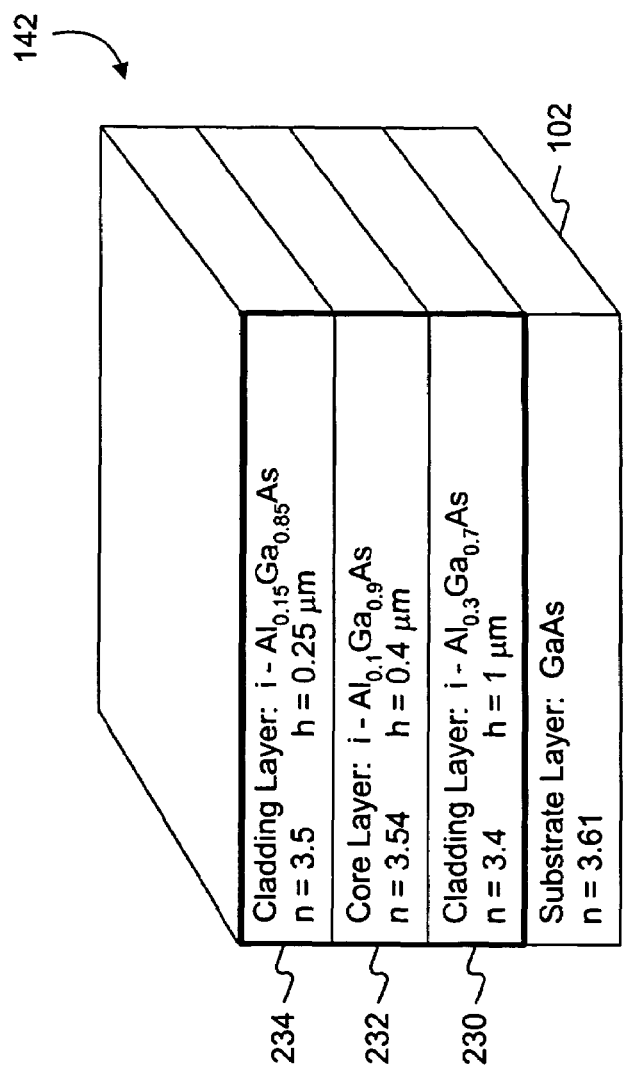

FIGS. 3D, 3E, and 3F show details of a photodiodes 120 and power splitter 142, respectively, for use in a system 100 according to an embodiment of the invention. As shown in FIG. 3D, optical fiber 117 may connect to power splitter via coupling 236. In one embodiment, coupling 236 may correspond to the mechanical connections shown in FIGS. 2A-2C. Photodiodes 120 and splitter 142 are designed such that photodiodes 120 produce an output of approximately 3.1 Volts and a current of greater than 3 mA upon receiving an input optical signal. The input optical signal may have a wavelength of 850 nm and a power of about 15 mW. FIG. 3D shows three photodiodes 120 producing approximately 1 Volt, which, when connected in series may then produce approximately 3.1 Volts.

As shown in FIG. 3E, an embodiment of a photodiode 120 may include a plurality of layers, including core, cladding, n-type, p-type, absorptive, and intrinsic layers. A cladding layer 202 comprised of AlGa may be formed adjacent substrate 102 (having n=3.4 and h=1 μm). The remainder of photodetector 120 may then proceed in the following adjacent layers: core layer 204 of AlGaAs (having n=3.54 and h=0.4 μm), cladding layer 206 of AlGaAs (having n=3.5 and h=0.25 μm), n-type layer 208 of AlGaAs (having n=3.4 and h=0.1 μm, and $[n]=4\times10^{18}/cm^3$), intrinsic layer 210 of AlGaAs (having n=3.4 and h=0.02 μm), absorptive layer 212 of GaAs (having n=3.61 and h=0.1 μm), intrinsic layer 214 of AlGaAs (having n=3.4 and h=0.02 μm), p-type layer 216 of AlGaAs (having n=3.4 and h=0.8 μm, and $[p]=1\times10^{18}/cm^3$), and p-type layer 218 of GaAs (having n=3.61 and h=0.03 μm, and $[p]=1\times10^{19}/cm^3$). Photodiode 120 preferably has a width of 6 μm, a length of 450 μm, and a height of 2.72 μm.

Photodiode 120 may be manufactured using any suitable semiconductor manufacturing techniques known in the art. For example, photodiode 120 may be manufactured using photolithography, wet etching, and contact deposition. A series of masks used to generate the structure may be designed using a CAD program. Etches sensitive to the aluminum content in AlGaAs may be used to allow individual layers to serve as etch stops as required.

In an embodiment using photodiode 120 shown in FIG. 3E, optical power enters from power splitter 142 through core layer 204 and is absorbed via evanescent power transfer in absorptive layer 212. Electrical contacts are then made to n-type and p-type layers 208, 216, and 218. A side contact is made to n-type layer 208. The total lateral resistance may be about 3 Ohms, generating a calculated resistive power loss of about 0.1% of the input power. Optical losses in the photovoltaic detector are simulated to be about 0.3% of the input power. Total power loss in detector 120 may thus be estimated to be about 0.4% of the input power.

Figure 3H:
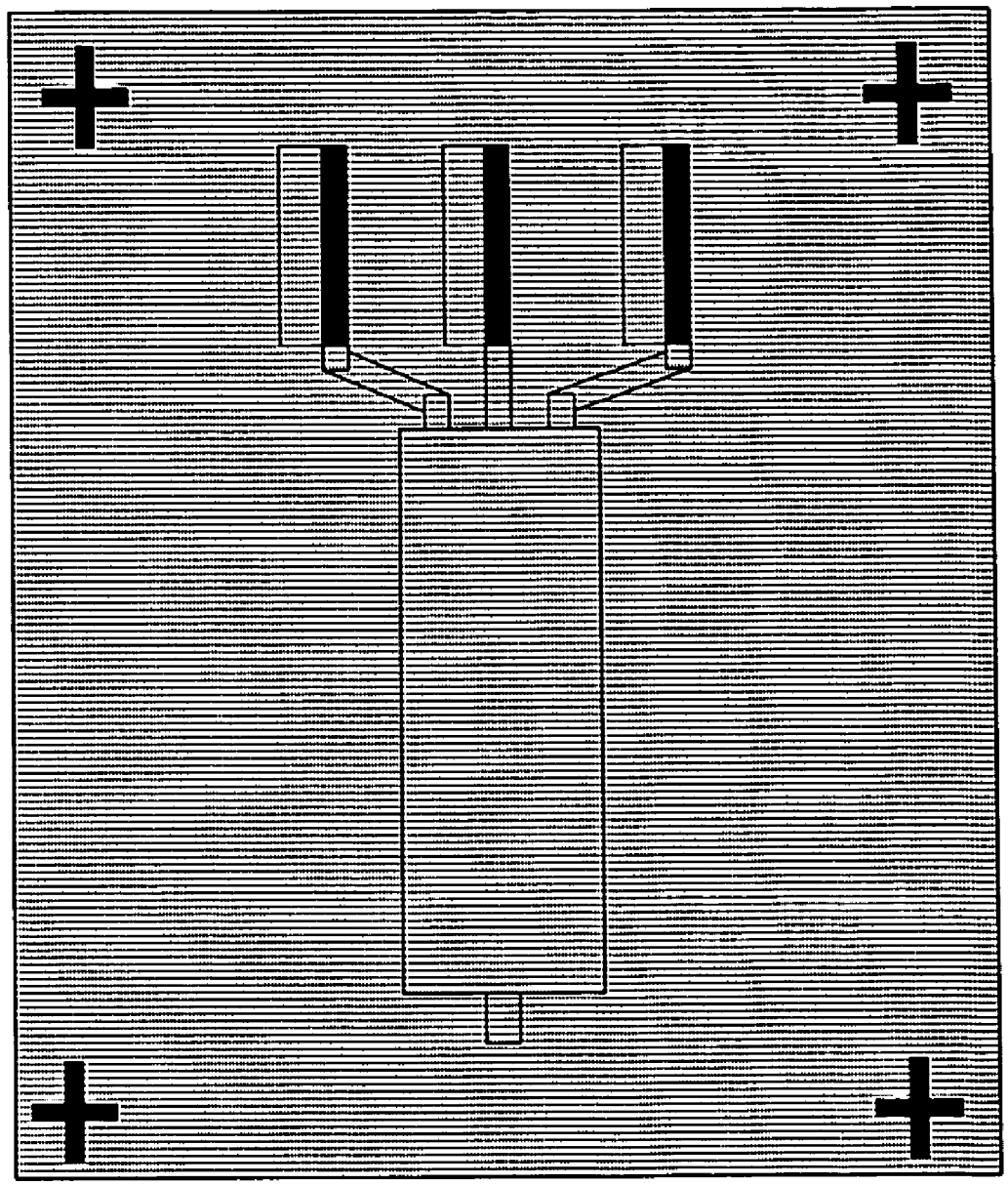
FIG. 3H shows an exemplary prototype mask for forming the power splitter during a semiconductor manufacturing process.

FIG. 3F shows details of an embodiment of power splitter 142 for use in a system 100 according to an embodiment of the invention. Power splitter 142 includes a multi-mode interference planar based waveguide coupler 236. In one exemplary embodiment, power splitter 142 may include a plurality of layers, including a cladding layer 230 (having n=3.4 and h=1 μm) adjacent substrate 102. Cladding layer is made of AlGaAs and is adjacent a core layer 232 made of AlGaAs (having n=3.54 and h=0.4 μm), which, in turn, is adjacent a cladding layer 234 made of AlGaAs (having n=3.5 and h=0.25 μm). Power splitter 142 preferably has a width of 40 μm, a length of 2.25 mm, and a height of 1.65 μm. Total power loss in power splitter 142 has been simulated to be about 4% of the input power. Optical power can enter power splitter 142 through an input waveguide 236 (see FIG. 3D). Waveguide 236, according to an embodiment, may be 6 μm by 150 μm. FIG. 3G illustrates the superior splitting detail of power splitter 142. Further, FIG. 3H shows an exemplary prototype mask for forming power splitter 142 during a semiconductor manufacturing process.

Figure 3I:
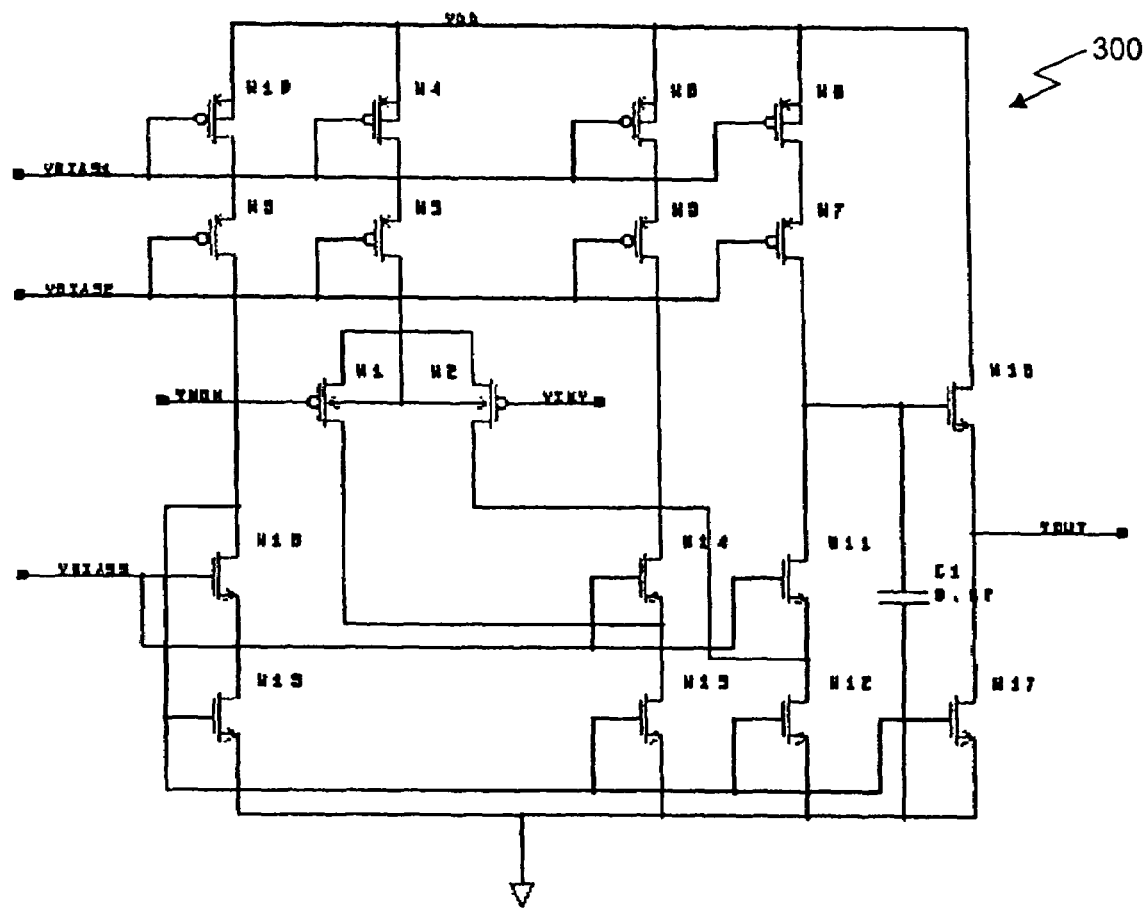
FIGS. 3I and 3J illustrate exemplary circuit diagrams of an amplifier 300 suitable for use in an implant system according to an embodiment of the invention.
Figure 3J:
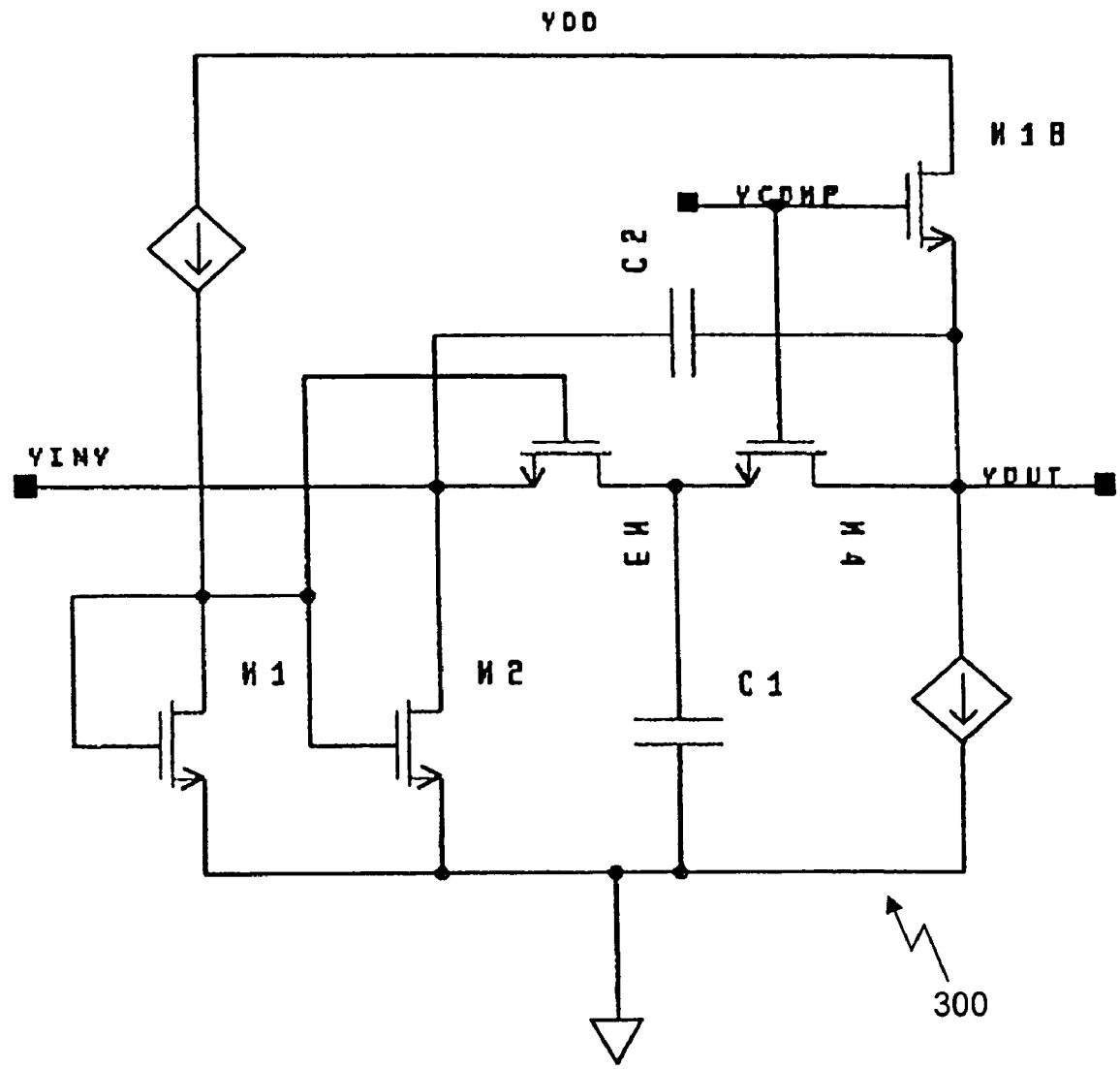

FIGS. 3I and 3J illustrate exemplary circuit diagrams of an amplifier 300 suitable for use in an implant system according to an embodiment of the invention, and particularly for system 100 shown in FIGS. 3A-3C. The amplifier shown and described in connection with these Figures is exemplary only and any other suitable amplifier may be used in implant systems according to embodiments of the invention. Amplifier 300 amplifies low amplitude signals, such as the neuron signals received from electrodes (e.g., probes 107) implanted near neurons of a brain. Amplifier 300 requires relatively low power and has relatively little noise. Further, for receiving neuron signals, amplifier 300 is preferably designed and selected to have a bandwidth of approximately 20 Hz to 10 kHz and a gain of about 800.

With respect to FIG. 3I, amplifier 300 may be based on folded cascode operation amplifier with a source follower output buffer. Amplifier 300 may include a feedback tee and a single pole source follower to provide a second order 7.5 kHz filter. Further, as shown in FIG. 3J, amplifier 300 may use MOSFETs for resistors as they require less fabrication space on chip 104. Transistors M3 and M4 of FIG. 3J are biased differently to provide linearity compensation. Transistor M18 is the source follower of amplifier 300, while transistors M2, M3, and M4 provide the feedback. Capacitors C1 and C2 define the two poles of the second-order filter, and biasing of transistor M1 can be shared between multiple amplifiers.

Figure 3K:
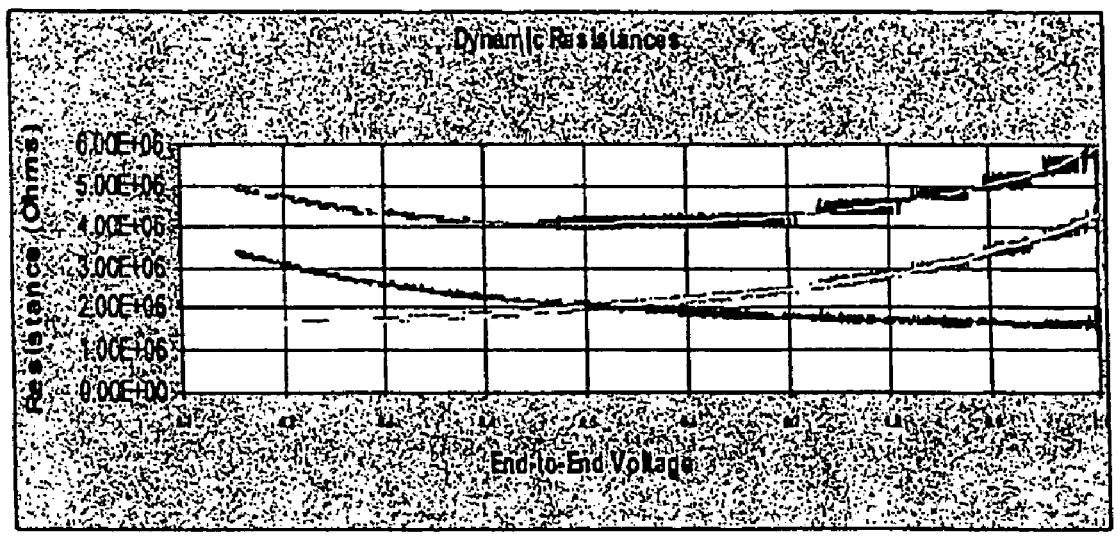
FIG. 3K shows the simulated performance of amplifier 300.
Figure 3K:
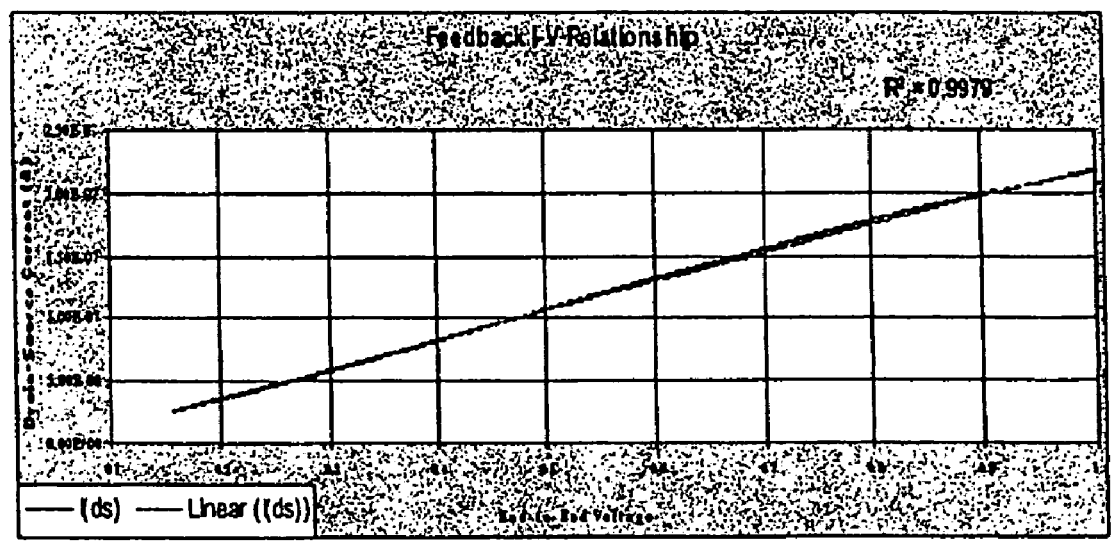

FIG. 3K shows the simulated performance of amplifier 300. As shown in FIG. 3K, the feedback of amplifier 300 has a linear response. Further, because amplifier requires a low power and limited bandwidth in one application of system 100, amplifier 300 may thus require a $4\times10^6$ Ohm equivalent input resistance. Amplifier 300 may satisfy such high resistance values, while requiring less fabrication space and thus a smaller overall size of chip 104.

In the embodiments described above with respect to FIGS. 3A-3C, optical fibers 114, 116, 117, 118 provide optical input directly to photodiodes 120. These fibers may branch from a single optical fiber communicating with an optical source or they may be entirely separate fibers that each individually communicate with the optical source. The optical fibers used in systems according to embodiments of the invention may be any fiber having suitable optical characteristics, including many commercially available optical fibers. In embodiments in which optical fibers are implanted into a body, the portion of the fibers in contact with any portion of the body or body fluid should be biocompatible.

Figure 3M:
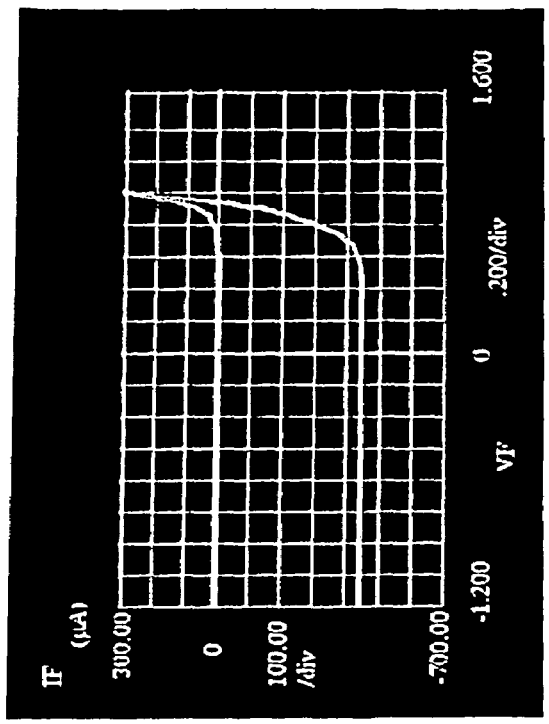
FIG. 3M illustrates a response characteristic of an arrangement illustrated by FIG. 3L.
Figure 3L:
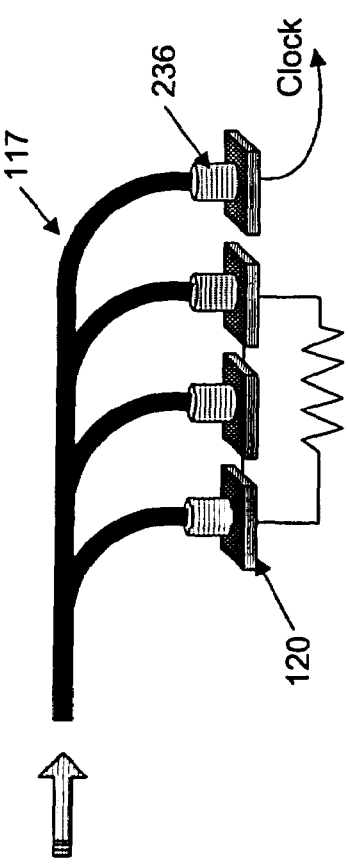
FIG. 3L illustrates an alternative arrangement for receiving power and other information signals over an optical cable.

For instance, FIG. 3L illustrates an alternative arrangement for receiving power and other information signals over an optical cable. As shown in FIG. 3L, a separate optical cable 117 may be coupled to a respective photodiode 120. While FIG. 3L shows four such photodiodes, any number may be used. Each photodiode 120 is coupled to the optical cable via a respective waveguide 236, as described above with respect to FIG. 3D, for example. In the exemplary embodiment of FIG. 3L, three of photodiodes 120 receive a power supply signal (e.g., a continuous stream of 840 nm pulses) over optical cable 117 and are thus connected in series to produce a combined voltage signal. The fourth photodiode 120 may receive a clock signal (e.g., a continuous stream of 850 nm pulses) for then outputting to chip 104. FIG. 3M illustrates a response characteristic of the arrangement illustrated by FIG. 3L.

According to embodiments of the invention, one or more implants may use UV light to prevent and/or reduce the likelihood of infection or may use a heat to provide a desired therapeutic effect (e.g., to increase cellular absorption of medicinal agent or drug). The heat may be converted from UV light provided to an implant via an optical fiber. Implants consistent with the invention may also employ direct photochemical conversion of the UV light into chemical neural triggers at a nerve cell region in the body where therapeutic action is desired. Such implants may be used in combination with one or more other implants that serve various other therapeutic or diagnostic functions.

For embodiments consistent with the invention that may use UV light to prevent and/or reduce the likelihood of infection, the UV light may be transmitted to a region within the body requiring treatment. Such a region may be where a malignancy was removed. By applying the UV light to these regions, the UV light could kill the cells in that region to prevent a recurrence of the malignancy.

As noted above, implants consistent with the present invention may also include magnetic therapy devices. When nanoscale magnetic particles are imbedded in the body near nerve cells (e.g., in the brain or elsewhere in the body), they generate electromagnetic impulses when the neural cells fire. These impulses can then be detected by the magnetic nanoparticles acting as a type of receiver. The nanoparticles, in turn, transmit these impulses to a magnetic receiver located external to the body, thus providing real-time diagnostics at the cellular level.

As described above, in the system 10 of FIG. 1, central implant 12 may serve as a UV source for one or more other implants 14 placed within the body and connected to UV source implant 12 through optical fibers 16. As shown in FIG. 1, certain implants 14 may connect directly to implant 12, while other implants 14 may connect to implant 12 through another implant 14 in a chain configuration. Optical fibers may couple to implants 14 through any suitable means, including those described herein, such as snap connections, suture connections, and screw connections. While the only implant configuration of FIG. 1 having a single implant within the chain is for the implant in the brain, a single implant 14 may also be directly coupled to implant 12 at any location within the body.

System 10 may include additional implants 12 to serve as additional UV sources for delivering UV light to the implants 14. All components of system 10 may be implanted. Alternatively, system 10 can include one or more transcutaneous optical fibers 18 that may connect to implant 12 to provide UV light that implant 12 disperses to the various implants 14. As a further alternative, one or more transcutaneous fibers can connect directly to implants 14 for delivery of UV light from an external source.

Figure 5A:
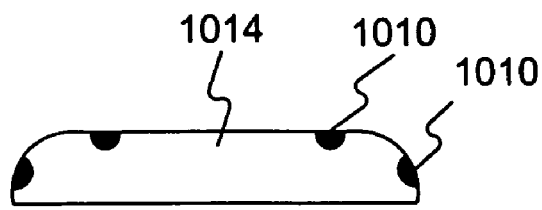
FIGS. 5A and 5B illustrate exemplary embodiments of an implant having structure for dispersing UV light, according to exemplary embodiments consistent with the invention.
Figure 5B:
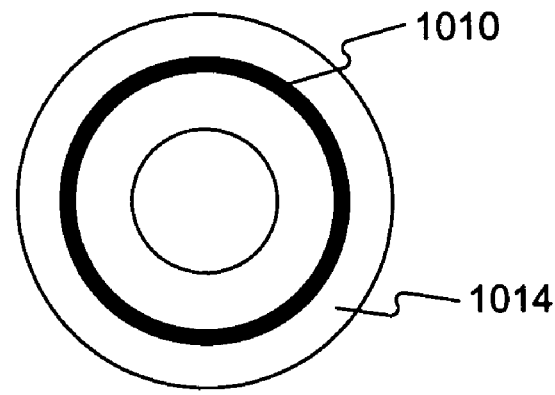

Each implant may include structure to disperse UV light to adjacent tissue in the body to prevent or reduce possible infection. According to an embodiment shown in FIGS. 5A and 5B, an implant 1014 may be disc-shaped with one or more diffusing rings 1010 that disperse UV light. Although shown as disc-shaped, the implant may have any shape for fitting in a desired location within the body and may include any suitable shaped diffusion element for targeting the dispersement of UV light to tissue of interest. The UV light can be continuous or pulse width modulated. The UV light could also be provided at, for example, a desired, predetermined amount of time each day. Diffusing rings 1010 may use a light scattering agent, such as titanium dioxide ($TiO_2$). The agent may be mixed in a transparent elastomer that is optically coupled with the optical fiber containing the UV light.

In embodiments using heat to provide a therapeutic effect, the implant may have any desired shape, such as a disc, and may have any number and shape of diffusion elements for dispersing heat. To disperse the heat, light can be sent to an assembly having an agent absorbing a predetermined wavelength of light (e.g., water absorbing light having a wavelength of 980 nm). The applied light heats the agent, which is then located in close proximity to the region to be treated by the implant. The implant assembly may include an opaque cover to prevent the escape of light. The implant itself may include suitable structure for converting light to electrical energy/heat or may be connected to any number of implants to serve those purposes.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for treating a body, comprising:
a first device configured to be implanted within the body,
an encapsulation covering substantially all of the first device to seal the first device from bodily fluids; and
an optical window associated with the first device and not covered by the encapsulation,
wherein a portion of the encapsulation is configured to mate with an optical fiber for optical coupling between the optical window and the optical fiber.

2. The system of claim 1, wherein the optical window is configured to communicate at least one of data and power with the optical fiber.

3. The system of claim 1, wherein the optical window is configured to communicate both data and power with the optical fiber.

4. The system of claim 1, further comprising an optical fiber configured for optical coupling to the optical window of the first device.

5. The system of claim 4, further comprising a connector associated with an end of the optical fiber, the connector configured to mate with the portion of the encapsulation to align the optical window with the end of the optical fiber.

6. The system of claim 4, further comprising a connector associated with an end of the optical fiber, the connector having a portion configured to receive the optical window and align the optical window with the end of the optical fiber.

7. The system of claim 6, wherein the connector includes at least one flange to engage the portion of the encapsulation and restrict removal of the connector from the encapsulation after engagement of the flange and the portion.

8. The system of claim 6, wherein the connector is configured to attach to the portion of the encapsulation with a connecting member.

9. The system of claim 1, wherein the first device includes an array of electrodes capable of sensing neural signals.

10. The system of claim 9, further comprising:
an optical fiber configured for optical coupling to the optical window of the first device; and
a second device configured for optical coupling to the optical fiber for transmission of at least one of data and power between the first device and the second device.

11. A system for treating a body, comprising:
a first device configured to be implanted within the body,
an encapsulation covering substantially all of the first device to seal the first device from bodily fluids;
an optical window associated with the first device and not covered by the encapsulation; and
a connector associated with an end of an optical fiber, the connector having a portion to receive the optical window and align the optical window with the end of the optical fiber,
wherein the connector includes at least one flange to engage a portion of the device and restrict removal of the connector from the device after engagement of the flange and the portion.

12. The system of claim 11, further comprising an optical fiber configured for optical coupling to the optical window of the first device.

13. The system of claim 12, wherein the connector is configured to mate with a portion of the encapsulation.

14. The system of claim 11, wherein the first device includes an array of electrodes capable of sensing neural signals.

15. The system of claim 14, further comprising:
   an optical fiber configured for optical coupling to the optical window of the first device; and
   a second device configured for optical coupling to the optical fiber for transmission of at least one of data and power between the first device and the second device.

16. The system of claim 11, wherein the optical window is configured to communicate at least one of data and power between the device and the optical fiber.

17. A system for treating a body, comprising:
   a first device configured to be implanted within the body,
   an encapsulation covering substantially all of the first device to seal the first device from bodily fluids;
   an optical window associated with the first device and not covered by the encapsulation; and
   a connector associated with an end of an optical fiber, the connector having a portion to receive the optical window and align the optical window with the end of the optical fiber,
   wherein the connector is configured to attach to the device with a suture.

18. The system of claim 17, further comprising an optical fiber configured for optical coupling to the optical window of the first device.

19. The system of claim 18, wherein the connector is configured to mate with a portion of the encapsulation to align the optical window with the end of the optical fiber.

20. The system of claim 17, wherein the first device includes an array of electrodes capable of sensing neural signals.

21. The system of claim 20, further comprising: p1 an optical fiber configured for optical coupling to the optical window of the first device; and
   a second device configured for optical coupling to the optical fiber for transmission of at least one of data and power between the first device and the second device.

22. The system of claim 17, wherein the optical window is configured to communicate at least one of data and power between the device and the optical fiber.

* * * * *

UNITED STATES PATENT AND TRADEMARK OFFICE
CERTIFICATE OF CORRECTION

PATENT NO. : 7,280,870 B2
APPLICATION NO. : 10/453785
DATED : October 9, 2007
INVENTOR(S) : Arto V. Nurmikko et al.

It is certified that error appears in the above-identified patent and that said Letters Patent is hereby corrected as shown below:

The entire claims (i.e., claims 1-22) starting at col. 14, line 11, should be replaced with the following claims:

1. A system for treating a body, comprising:
a first device configured to be implanted within the body,
an encapsulation covering substantially all of the first device to seal the first device from bodily fluids;
an optical window associated with the first device and not covered by the encapsulation;
an optical fiber configured for optical coupling to the optical window of the first device; and
a connector associated with an end of the optical fiber, the connector having a portion configured to receive the optical window and align the optical window with the end of the optical fiber,
wherein a portion of the encapsulation is configured to mate with an optical fiber for optical coupling between the optical window and the optical fiber.

2. The system of claim 1, wherein the connector includes at least one flange to engage the portion of the encapsulation and restrict removal of the connector from the encapsulation after engagement of the flange and the portion.

3. The system of claim 1, wherein the connector is configured to attach to the portion of the encapsulation with a connecting member.

4. The system of claim 1, wherein the connector is configured to mate with the portion of the encapsulation to align the optical window with the end of the optical fiber.

5. The system of claim 1, wherein the first device includes an array of electrodes capable of sensing neural signals.

6. The system of claim 5, further comprising:
a second device configured for optical coupling to the optical fiber for transmission of at least one of data and power between the first device and the second device.

UNITED STATES PATENT AND TRADEMARK OFFICE
CERTIFICATE OF CORRECTION

PATENT NO. : 7,280,870 B2
APPLICATION NO. : 10/453785
DATED : October 9, 2007
INVENTOR(S) : Arto V. Nurmikko et al.

It is certified that error appears in the above-identified patent and that said Letters Patent is hereby corrected as shown below:

7. The system of claim 1, wherein the optical window is configured to communicate at least one of data and power with the optical fiber.

8. The system of claim 1, wherein the optical window is configured to communicate both data and power with the optical fiber.

9. A system for treating a body, comprising:
a first device configured to be implanted within the body,
an encapsulation covering substantially all of the first device to seal the first device from bodily fluids;
an optical window associated with the first device and not covered by the encapsulation; and
a connector associated with an end of an optical fiber, the connector having a portion to receive the optical window and align the optical window with the end of the optical fiber,
wherein the connector includes at least one flange to engage a portion of the device and restrict removal of the connector from the device after engagement of the flange and the portion.

10. The system of claim 9, further comprising an optical fiber configured for optical coupling to the optical window of the first device.

11. The system of claim 10, wherein the connector is configured to mate with a portion of the encapsulation.

12. The system of claim 9, wherein the first device includes an array of electrodes capable of sensing neural signals.

13. The system of claim 12, further comprising:
an optical fiber configured for optical coupling to the optical window of the first device; and
a second device configured for optical coupling to the optical fiber for transmission of at least one of data and power between the first device and the second device.

14. The system of claim 9, wherein the optical window is configured to communicate at least one of data and power between the device and the optical fiber.

UNITED STATES PATENT AND TRADEMARK OFFICE
CERTIFICATE OF CORRECTION

| | |
|---|---|
| PATENT NO. | : 7,280,870 B2 |
| APPLICATION NO. | : 10/453785 |
| DATED | : October 9, 2007 |
| INVENTOR(S) | : Arto V. Nurmikko et al. |

It is certified that error appears in the above-identified patent and that said Letters Patent is hereby corrected as shown below:

15. A system for treating a body, comprising:
a first device configured to be implanted within the body,
an encapsulation covering substantially all of the first device to seal the first device from bodily fluids;
an optical window associated with the first device and not covered by the encapsulation; and
a connector associated with an end of an optical fiber, the connector having a portion to receive the optical window and align the optical window with the end of the optical fiber,
wherein the connector is configured to attach to the device with a suture.

16. The system of claim 15, further comprising an optical fiber configured for optical coupling to the optical window of the first device.

17. The system of claim 16, wherein the connector is configured to mate with a portion of the encapsulation to align the optical window with the end of the optical fiber.

18. The system of claim 15, wherein the first device includes an array of electrodes capable of sensing neural signals.

UNITED STATES PATENT AND TRADEMARK OFFICE
CERTIFICATE OF CORRECTION

PATENT NO.       : 7,280,870 B2
APPLICATION NO.  : 10/453785
DATED            : October 9, 2007
INVENTOR(S)      : Arto V. Nurmikko et al.

It is certified that error appears in the above-identified patent and that said Letters Patent is hereby corrected as shown below:

19. The system of claim 18, further comprising:
an optical fiber configured for optical coupling to the optical window of the first device; and
a second device configured for optical coupling to the optical fiber for transmission of at least one of data and power between the first device and the second device.

20. The system of claim 15, wherein the optical window is configured to communicate at least one of data and power between the device and the optical fiber.

Signed and Sealed this

Thirty-first Day of March, 2009

JOHN DOLL
*Acting Director of the United States Patent and Trademark Office*